(12) United States Patent
Ridder et al.

(10) Patent No.: US 7,848,605 B2
(45) Date of Patent: Dec. 7, 2010

(54) METHOD OF MAKING OPTICAL PROBES FOR NON-INVASIVE ANALYTE MEASUREMENTS

(75) Inventors: Trent Ridder, Tucson, AZ (US); Ben ver Steeg, Redlands, CA (US); Mike Mills, Tijeras, NM (US)

(73) Assignee: TruTouch Technologies, Inc., Albuquerque, NM (US)

( * ) Notice: Subject to any disclaimer, the term of this patent is extended or adjusted under 35 U.S.C. 154(b) by 305 days.

(21) Appl. No.: 12/185,224

(22) Filed: Aug. 4, 2008

(65) Prior Publication Data

US 2009/0003764 A1 Jan. 1, 2009

Related U.S. Application Data

(63) Continuation-in-part of application No. 11/305,964, filed on Dec. 19, 2005, now Pat. No. 7,756,558, which is a continuation-in-part of application No. 10/852,415, filed on May 24, 2004, now Pat. No. 7,403,804.

(51) Int. Cl.
G02B 6/44 (2006.01)

(52) U.S. Cl. .................... 385/114; 385/100; 385/115; 385/901

(58) Field of Classification Search .......... 385/100, 385/114, 115, 901
See application file for complete search history.

(56) References Cited

U.S. PATENT DOCUMENTS

| | | | |
|---|---|---|---|
| 4,975,581 A | 12/1990 | Robinson et al. | |
| 5,830,112 A | 11/1998 | Wang et al. | |
| 5,953,477 A | 9/1999 | Watch et al. | |
| 6,006,001 A | 12/1999 | Alfano et al. | |
| 6,157,041 A | 12/2000 | Thomas et al. | |
| 6,219,565 B1 | 4/2001 | Cupp et al. | |
| 6,411,373 B1 | 6/2002 | Garside et al. | |
| 6,622,032 B1 | 9/2003 | Robinson et al. | |
| 6,678,541 B1 | 1/2004 | Durkin et al. | |
| 6,684,099 B2 | 1/2004 | Ridder et al. | |
| 6,870,620 B2 | 3/2005 | Faupel et al. | |
| 6,939,313 B2 * | 9/2005 | Saadat et al. | ................ 600/587 |
| 7,139,076 B1 | 11/2006 | Marbach | |
| 7,348,786 B2 * | 3/2008 | Thacker et al. | ............... 324/754 |

* cited by examiner

*Primary Examiner*—Jennifer Doan
(74) *Attorney, Agent, or Firm*—V. Gerald Grafe

(57) ABSTRACT

An optical probe for non-invasively measuring an analyte property in a biological sample of a subject, comprises a plurality of illumination fibers that deliver source light from an optical probe input to a sample interface, a plurality of collection fibers that deliver light returned from the sample interface to an optical probe output, and wherein the illumination and collection fibers are oriented substantially perpendicular to the sample interface and the illumination and collection fibers are stacked in a plurality of linear rows to provide a stack of fibers arranged in a rectangular pattern. The optical probe is amenable to manufacturing on a scale consistent with a commercial product. Methods of making such probes are described.

20 Claims, 42 Drawing Sheets

Input (280 fibers)

METHOD OF MAKING OPTICAL PROBES FOR NON-INVASIVE ANALYTE MEASUREMENTS

CROSS REFERENCE TO RELATED APPLICATIONS

This application claims priority under 35 U.S.C §120 as a continuation-in-part of U.S. patent application Ser. No. 11/305,964, entitled "Apparatus and Methods for Mitigating the Effects of Foreign Interferents on Analyte Measurements in Spectroscopy," filed Dec. 19, 2005, which application was a continuation-in-part of U.S. patent application Ser. No. 10/852,415, entitled "Noninvasive determination of alcohol in tissue," filed May 24, 2004, now U.S. Pat. No. 7,403,804, each of which is incorporated herein by reference.

FIELD OF THE INVENTION

The present invention generally relates to optical probe designs for the measurement one or more analytes of interest in vivo.

BACKGROUND OF THE INVENTION

The present invention predominantly deals with non-invasive determination of attributes in humans or human samples by quantitative spectroscopy. Spectroscopy offers the potential of completely non-invasive measurements for a variety of applications such as alcohol monitoring, glucose monitoring, diagnostic medicine, quality control, and process monitoring. Non-invasive measurements that use quantitative spectroscopy are desirable because they are painless, do not require a fluid draw from the body, carry little risk of contamination or infection, do not generate any hazardous waste, and can have short measurement times. Quantitative spectroscopy can measure a variety of attributes of interest including, as examples, analyte presence, analyte concentration (e.g., alcohol or substance of abuse concentration), direction of change of an analyte concentration, rate of change of an analyte concentration, disease presence (e.g., alcoholism or diabetes), disease state, and combinations and subsets thereof.

Several approaches have been proposed for the non-invasive determination of attributes in humans or human samples. These systems have included technologies incorporating polarimetry, mid-infrared spectroscopy, Raman spectroscopy, Kromoscopy, fluorescence spectroscopy, nuclear magnetic resonance spectroscopy, radio-frequency spectroscopy, ultrasound, transdermal measurements, photo-acoustic spectroscopy, and near-infrared spectroscopy. Many of these approaches share a common need to deliver light to and collect light from the sample of interest. The sample of interest can be skin tissue of a subject, biopsied tissue, internal tissues accessed by an endoscope, blood, saliva, urine, or any other biological tissue of interest. In the context of non-invasive measurements, the part of a system that delivers and collects the light is often referred to as an optical probe or an optical sampler. One skilled in the art recognizes that other terms may exist that refer to a system component that serves this purpose.

Many systems for non-invasive measurement of analytes are known in the art, several of which describe embodiments of optical probes for measuring analytes in biological samples. As an example, Robinson et al. in U.S. Pat. No. 4,975,581 disclose a method and apparatus for measuring a characteristic of unknown value in a biological sample using infrared spectroscopy in conjunction with a multivariate model that is empirically derived from a set of spectra of biological samples of known characteristic values. The above-mentioned characteristic is generally the concentration of an analyte, such as alcohol, but also can be any chemical or physical property of the sample. The method of Robinson et al. involves a two-step process that includes both calibration and prediction steps.

In the calibration step, the infrared light is coupled to calibration samples of known characteristic values so that there is attenuation of at least several wavelengths of the infrared radiation as a function of the various components and analytes comprising the sample with known characteristic value. The infrared light is coupled to the sample by passing the light through the sample or by reflecting the light off the sample. Absorption of the infrared light by the sample causes intensity variations of the light that are a function of the wavelength of the light. The resulting intensity variations at a minimum of several wavelengths are measured for the set of calibration samples of known characteristic values. Original or transformed intensity variations are then empirically related to the known characteristics of the calibration samples using multivariate algorithms to obtain a multivariate calibration model.

In the prediction step, the infrared light is coupled to a sample of unknown characteristic value, and a multivariate calibration model is applied to the original or transformed intensity variations of the appropriate wavelengths of light measured from this unknown sample. The result of the prediction step is the estimated value of the characteristic of the unknown sample. The disclosure of Robinson et al. is incorporated herein by reference.

A further method of building a calibration model and using such model for prediction of analytes and/or attributes of tissue is disclosed in commonly assigned U.S. Pat. No. 6,157,041 to Thomas et al., entitled "Method and Apparatus for Tailoring Spectrographic Calibration Models," the disclosure of which is incorporated herein by reference.

In U.S. Pat. No. 5,830,112, Robinson describes a general method of robust sampling of tissue for non-invasive analyte measurement. The sampling method utilizes a tissue-sampling accessory that is pathlength optimized by spectral region for measuring an analyte such as alcohol. The patent discloses several types of spectrometers for measuring the spectrum of the tissue from 400 to 2500 nm, including acousto-optical tunable filters, discrete wavelength spectrometers, filters, grating spectrometers and FTIR spectrometers. The disclosure of Robinson is incorporated hereby reference.

Although there has been substantial work conducted in attempting to produce commercially viable non-invasive spectroscopy-based systems for determination of attributes in humans and human samples, several challenges remain. It is believed that the systems described in the prior art have had limited success because of the challenges imposed by the spectral characteristics of tissue which make the design of a commercially viable measurement system a formidable task. Thus, there is a substantial need for a commercially viable device which incorporates subsystems and methods with sufficient accuracy and precision to make clinically relevant determinations of biological attributes in human tissue. The present invention is primarily concerned with the optical probe, which is one of the system components that influence commercial viability of a non-invasive measurement system.

In U.S. Pat. No. 5,953,477, Wach et al. disclose embodiments of optical fiber treatments that serve to improve the efficiency of optical probes. The treatments include reflective surfaces coatings applied to fibers that have been ground or shaped to alter the light output or collection properties of the fiber at the sample interface. Wach et al. also disclose the application of optical filtering materials directly to the ends of the optical fibers at sample interface. All of the embodiments involve a central fiber surrounded by a circular arrangement of additional fibers with at least one having a shaped end or internally reflective surfaces to bend or steer the emitted or collected light paths from its longitudinal axis (e.g., the axis parallel to the optical fiber and perpendicular to the sample interface). None of the embodiments disclosed in the present invention involve circular arrangements at the sample interface, shaping the ends of any fibers, or internally reflective surfaces to steer or bend light paths.

In U.S. Pat. No. 6,006,001 Alfano et al. disclose embodiments of optical probes suitable for endoscopy. All disclosed embodiments are comprised of illumination and collection fibers encased in a tubular structure and include a narrow band filter between the illumination and collection fibers. None of the embodiments disclosed in the present invention involve tubular encasing structures or narrow band filters.

In U.S. Pat. No. 6,219,565 Cupp et al. discloses optical probes for measuring glucose. All independent claims are limited to glucose and ring geometries (illumination fibers surround each collection fiber in a circular pattern). None of the embodiments of the present invention involve ring illumination/collection geometries.

In U.S. Pat. No. 6,411,373, Garside et al. disclose fiber optic illumination and detection patterns for use in spectroscopic analysis. They disclose a design process for determining the illumination-detection pattern at the sample interface. The ratio of the illumination to detector fibers in the disclosed embodiments is restricted by the size of the fiber bundle at the detector. The embodiments of the present invention are not subject to this restriction. Furthermore, Garside et al. disclose optical probe embodiments incorporating hex-packed fibers. None of the embodiments disclosed in the present invention involve hex-packed optical fibers at the sample interface. Garside et al, further disclose a design method that states "fabrication constraints should be ignored whenever possible", and as such, is a starkly contrasting approach to that of the present invention.

In U.S. Pat. No. 6,678,541, Durkin et al. disclose optical probe geometries for measuring optical properties, such as the scattering coefficient of a sample. A single illumination channel is used to sequentially measure the sample at multiple collection channels at different separations relative to the illumination channel. A function relating the change in signal to illumination/collection separation is then used to determine the optical property of interest. No embodiments of the present invention involve determining properties by examining signals as a function of illumination/collection separation.

In U.S. Pat. No. 6,870,620, Faupel et al. disclose optical probe embodiments that are predominantly suited to fluorescence spectroscopy. All of the embodiments involve translating, rotating, or repositioning the optical probe during a measurement or a sample interface surface that conforms to the shape of the sample being measured. None of the embodiments of the present invention involve rotating, translating, or otherwise moving the optical probe. Furthermore, none of the embodiments of the present invention involve sample interfaces that conform to the sample shape. In the embodiments of the present invention, the sample interface is polished flat.

In U.S. Pat. No. 7,136,076, Marbach discloses multi-channel optical probes for cancelling out surface effects of samples. Marbach does not disclose the advantages of or motivations for using multi-channel optical probes other than compensating for surface effects. For example, inducing multiple pathlengths through a sample using a multi-channel probe can provide insight into the pathlengths of each channel that might be obfuscated if only a single channel measurement were performed. Furthermore, all independent claims incorporate the explicit step of using algorithms or equations to process the measured channels in order to cancel surface effects. None of the embodiments of the present invention involve algorithms or equations to explicitly cancel surface effects.

SUMMARY OF THE INVENTION

Any design of an optical probe suitable for non-invasive measurements must consider several variables such as the efficiency of coupling or throughput of light into and out of the sample, depth of penetration into the sample, quality of interface with the sample (e.g., effects of hair and wrinkles), spatial and angular homogeneity of the light introduced and collected from the sample, the wavelengths of light under consideration, and the surface quality of the optical probe. Each of these variables contributes to the overall performance of the probe. However, the performance of the optical probe is only one consideration for a commercially viable non-invasive measurement system.

The optical probe design must also be amenable to manufacturing on a scale consistent with a commercial product. This aspect of optical probe design has generally not been considered in the art despite the fact it is a critical enabling aspect of a non-invasive measurement system. The present invention discloses a family of optical probes that optimize the trade between performance and manufacturing objectives. This balance provides optical probes that offer sufficient measurement performance while enabling reproducible and scalable high volume manufacturing.

A significant requirement for a manufacturable design is the ability to cost-effectively measure and verify subassemblies earlier in the manufacturing process, thereby reducing failure rates during final assembly. The current invention offers a significant improvement over designs disclosed in the art that are labor intensive to fabricate and difficult to verify prior to completion. The optical probes of the present invention also offer improved physical robustness to contamination from the environments encountered in non-invasive measurements. In addition, some embodiments within the family of disclosed designs are comprised of optical materials that offer substantial performance advantages relative to commonly available optical fibers typically used in optical probe fabrication.

The subsystems of the non-invasive monitor are highly optimized to provide reproducible and, preferably, uniform illumination of the tissue, low tissue sampling error, depth targeting of the tissue layers that contain the property (analyte) of interest, and efficient collection of diffuse reflectance spectra from the tissue.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1:
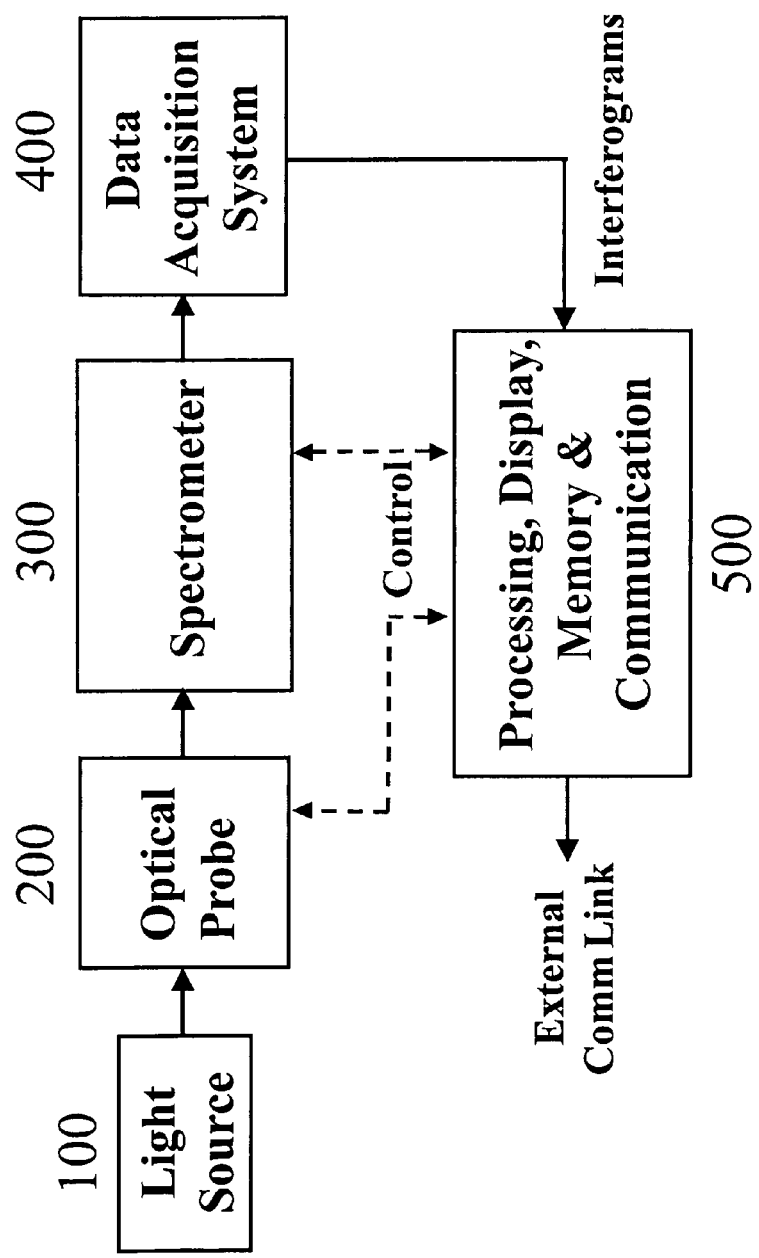
FIG. 1 is a diagram of a non-invasive analyte measurement system showing an illumination, optical probe, and spectrometer subsystem orientation.

For the purposes of this invention, the term "analyte concentration" generally refers to the concentration of an analyte, such as alcohol. The term "analyte property" includes analyte concentration and other properties, such as the presence or absence of the analyte or the direction or rate of change of the analyte concentration, or a biometric, which can be measured in conjunction with or instead of the analyte concentration. While the disclosure generally references alcohol as the "analyte" of interest, other chemicals, including but not limited to substances of abuse, alcohol biomarkers, and alcohol byproducts, can also benefit from the present invention. The term "alcohol" is used as an example analyte of interest; the term is intended to include ethanol, methanol, ethyl glycol or any other chemical commonly referred to as alcohol. For the purposes of this invention, the term "alcohol byproducts" includes the adducts and byproducts of the metabolism of alcohol by the body including, but not limited to, acetone, acetaldehyde, and acetic acid. The term "alcohol biomarkers" includes, but is not limited to, Gamma Glutamyl Transferase (GGT), Aspartate Amino Transferase (AST), Alanine Amino Transferase (ALT), Mean Corpuscular Volume (MCV), Carbohydrate-Deficient Transferrin (CDT), Ethyl Glucuronide (EtG), Ethyl Sulfate (EtS), and Phosphatidyl Ethanol (PEth). The term "substances of abuse" refers to, but is not limited to, THC (Tetrahydrocannabinol or marijuana), cocaine, M-AMP (methamphetamine), OPI (morphine and heroin), OxyContin, Oxycodone, and PCP (phencyclidine). The term "biometric" refers to an analyte or biological characteristic that can be used to identify or verify the identity of a specific person or subject.

The present invention addresses this need for analyte measurements of samples utilizing spectroscopy where the term "sample" generally refers to biological tissue. The term "subject" generally refers to a person from whom a sample measurement was acquired.

For the purposes of this invention the term "dispersive spectrometer" indicates a spectrometer based upon any device, component, or group of components that spatially separate one or more wavelengths of light from other wavelengths. Examples include, but are not limited to, spectrometers that use one or more diffraction gratings, prisms, holographic gratings. For the purposes of this invention the term "interferometric/modulating spectrometer" indicates a class of spectrometers based upon any device, component, or group of components that either modulate different wavelengths of light to different frequencies in time or selectively transmits or reflects certain wavelengths of light based upon the properties of light interference. Examples include, but are not limited to, Fourier transform interferometers, Hadamard spectrometers, Sagnac interferometers, mock interferometers, Michelson interferometers, one or more etalons, acousto-optical tunable filters (AOTF's), and one or more LED's or VCSEL's that are scanned or modulated. One skilled in the art recognizes that spectrometers based on combinations of dispersive and interferometric/modulating properties, such as those based on lamellar gratings, are also suitable for the present invention.

The invention makes use of "signals", described in some of the examples as absorbance or other spectroscopic measurements. Signals can comprise any measurement obtained concerning the spectroscopic measurement of a sample or change in a sample, e.g., absorbance, reflectance, intensity of light returned, fluorescence, transmission, Raman spectra, or various combinations of measurements, at one or more wavelengths. Some embodiments make use of one or more models, where such a model can be anything that relates a signal to the desired property. Some examples of models include those derived from multivariate analysis methods, such as partial least squares regression (PLS), linear regression, multiple linear regression (MLR), classical least squares regression (CLS), neural networks, discriminant analysis, principal components analysis (PCA), principal components regression (PCR), cluster analysis, and K-nearest neighbors. Single or multi-wavelength models based on the Beer-Lambert law are special cases of classical least squares and are thus included in the term multivariate analysis for the purposes of the present invention.

The following detailed description should be read with reference to the drawings. The drawings, which are not necessarily to scale, depict illustrative embodiments that are not intended to limit the scope of the invention. For the purposes of the application, the term "about" applies to all numeric values, whether or not explicitly indicated. The term "about" generally refers to a range of numbers that one of skill in the art would consider equivalent to the recited value (i.e., having the same function or result). In some instances, the term "about" can include numbers that are rounded to the nearest significant figure.

System Overview

Figure 2:
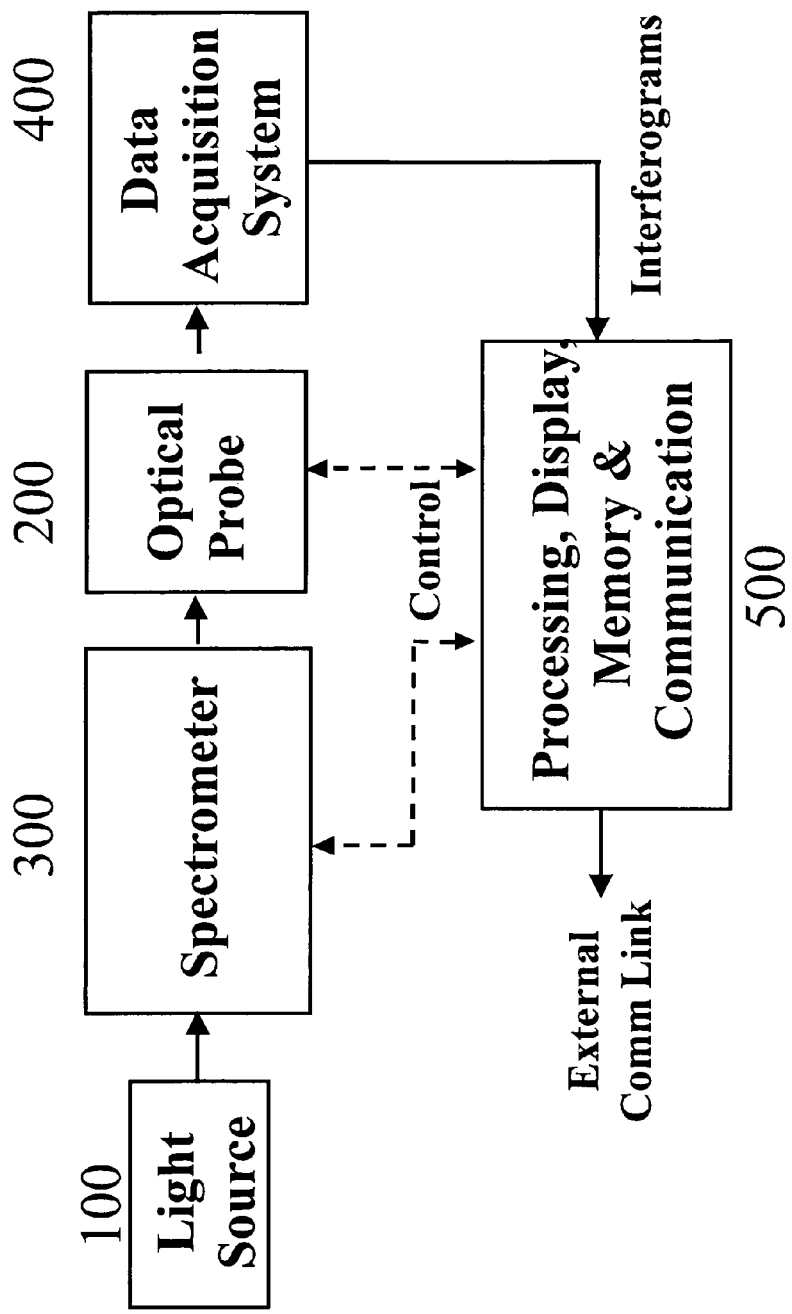
FIG. 2 is a diagram of a non-invasive analyte measurement system showing an illumination, spectrometer, and optical probe subsystem orientation.

FIGS. 1 and 2 show diagrams of non-invasive analyte measurement systems. Each figure is comprised of the basic subsystems that collectively form a measurement system. FIGS. 1 and 2 indicate that the orientation of the optical probe (200) can be either between the illumination (100) and spectrometer (300) subsystems or between the spectrometer (300) and data acquisition (400) subsystems.

Figure 3:
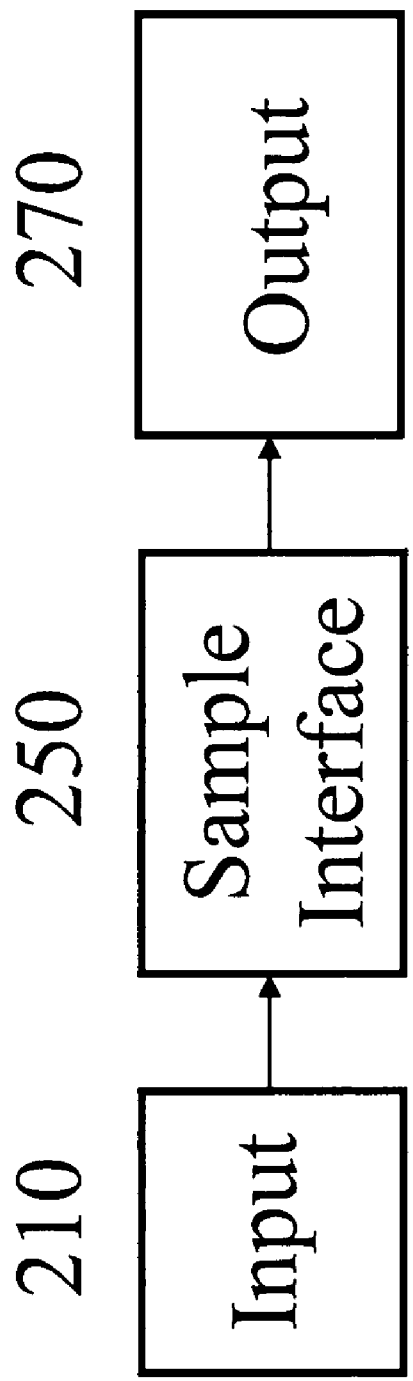
FIG. 3 is a diagram showing the key aspects of an optical probe.

While the subsequent discussion focuses on the illumination/sampling/FTIR subsystem orientation, it should not be interpreted as limiting. Referring to FIG. 1, the optical probe subsystem (200) introduces radiation generated by the illumination subsystem (100) into the sample, collects a portion of the radiation not absorbed by the sample and sends that radiation to the spectrometer subsystem (300) for measurement and processing by the data acquisition subsystem (400). Regardless of the orientation in FIGS. 1 and 2, the optical probe (200) has an input (210), a sample interface (250), and an output (270) as shown in FIG. 3. One skilled in the art recognizes that orientations other than those shown in FIGS. 1 and 2 are possible and that the present invention is equally suitable in those cases. The remainder of the disclosure will focus on the optical probe (200).

Example of Optical Probe Known in the Art

Figure 4:
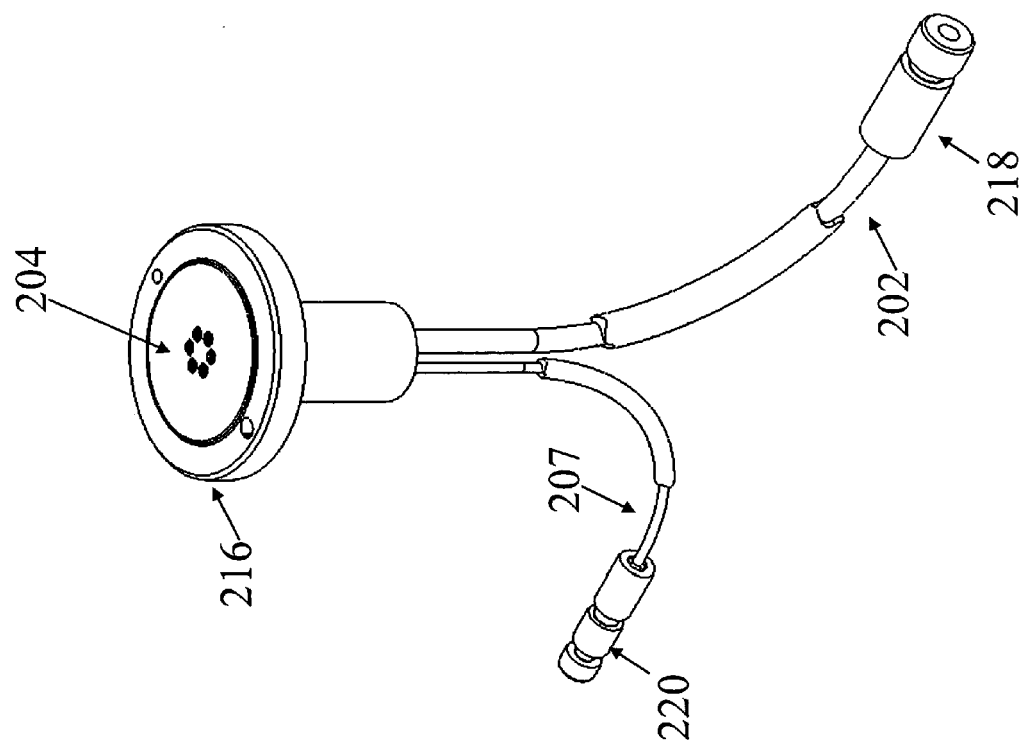
FIG. 4 is a diagram of an optical probe known in the art.
Figure 5:
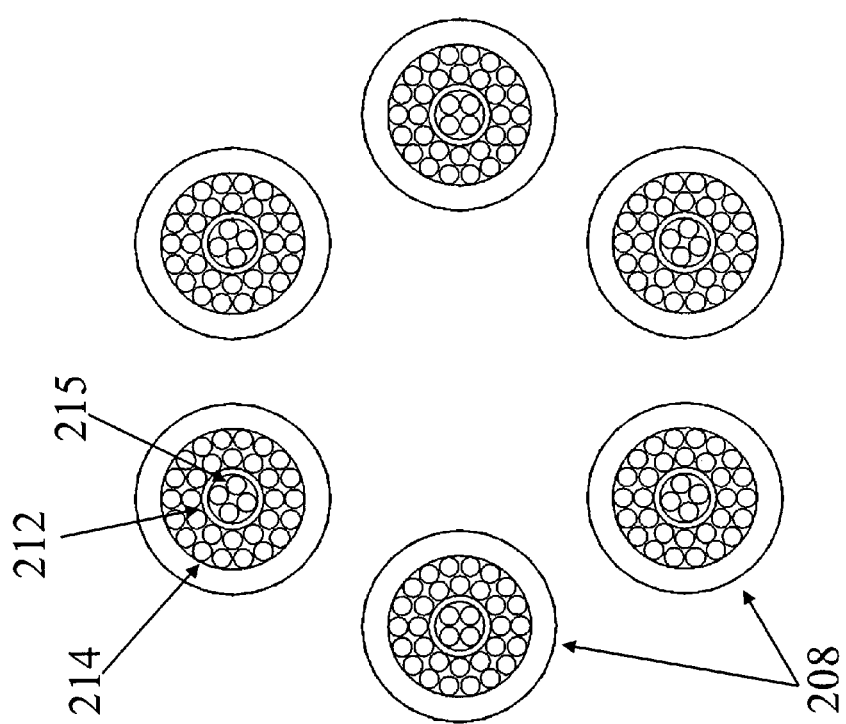
FIG. 5 is a magnified view of the sample interface of the known optical probe shown in FIG. 4.

FIG. 4 shows a diagram of an optical probe that is known in the art. As with the generic optical probe shown in FIG. 3, this known optical probe has an input (202), an output (207), and a sample interface (204). The optical input is comprised of a bundle of 200 µm diameter optical fibers that collects light from an illumination subsystem. FIG. 5 shows a magnified view of the sample interface (204) of the known optical probe which depicts the ends of the input and output fibers in a six cluster (208) geometry arranged in a circular pattern. In essence, the bundle of input fibers (202) is re-oriented at the sample interface (204) to deliver light to the sample via a ring of illumination fibers (214 in FIG. 5) in a controlled geometry. Each cluster in FIG. 5 includes four central collection fibers (215) which collect light returned from the sample. Around each grouping of four central collection fibers (215) is a cylinder of material (212) which ensures a 100-µm gap between the edges of the central collection fibers (215) and the outer ring of illumination fibers (214). The 100-µm gap can be important to prevent unwanted short-path light from being collected by the collection fibers. In this design, the collection fibers (215) are then collected into an output bundle (207) to transmit the light to either the spectrometer subsystem (300) or data acquisition subsystem (400) depending on the system orientation.

While the known optical probe depicted in FIGS. 4 and 5 can provide suitable measurement performance, it has several practical disadvantages. First, the cluster geometry requires precision machined parts in order to ensure that each of the 6 clusters is appropriately located at the sample interface. Furthermore, the circular pattern of illumination and collection fibers with a 100-µm gap within each cluster requires careful alignment of each fiber relative to each other and the gap. Clearly, such tolerances are labor intensive, potentially difficult to reproduce, and prone to a high failure rate. The present invention discloses a family of optical probes that achieve similar or superior performance while significantly alleviating many of the fabrication limitations imposed by designs known in the art. The designs are scalable in terms of physical size (to accommodate different sample sizes or locations) as well as production volume. Furthermore, several optical materials are disclosed for use in optical probes that offer superior performance for non-invasive analyte measurements. When combined with the optical probes of the present invention, the disclosed optical materials enable simultaneous performance and manufacturing improvements. The family of optical probes of the present invention will be discussed in terms of input, sample interface, and output; consistent with the terms used to describe the generic optical probe in FIG. 3.

Optical Probe Input

Input and Output Aperture Matching

In the present invention, optical fibers are used to collect light from a light source or illumination subsystem (100) and transfer the light to the sample interface. These fibers will be referred to as the "illumination" fibers. The total number of potential illumination fibers can depend on the physical size of emissive area of the light source or illumination subsystem (100), the diameter of each fiber, and the size and overall geometry of the fibers at the sample interface. In some embodiments, the emissive area of the light source can exceed that of the illumination portion of the sample interface. In others, the illumination area of the sample interface can be larger or equal to that of the emissive area of the light source. In some systems, multiple light sources can be used to increase the emissive area. Regardless, the geometry of the illumination fibers where it meets the light source or illumination subsystem (100) can be a circular, square, or other shaped bundle such that it is consistent with the output of the light source or illumination subsystem. In a similar fashion, if the optical probe is used in a system with the orientation shown in FIG. 2, the geometry of the illumination fibers would be such that it matches the output of the spectrometer subsystem (300).

Figure 6:
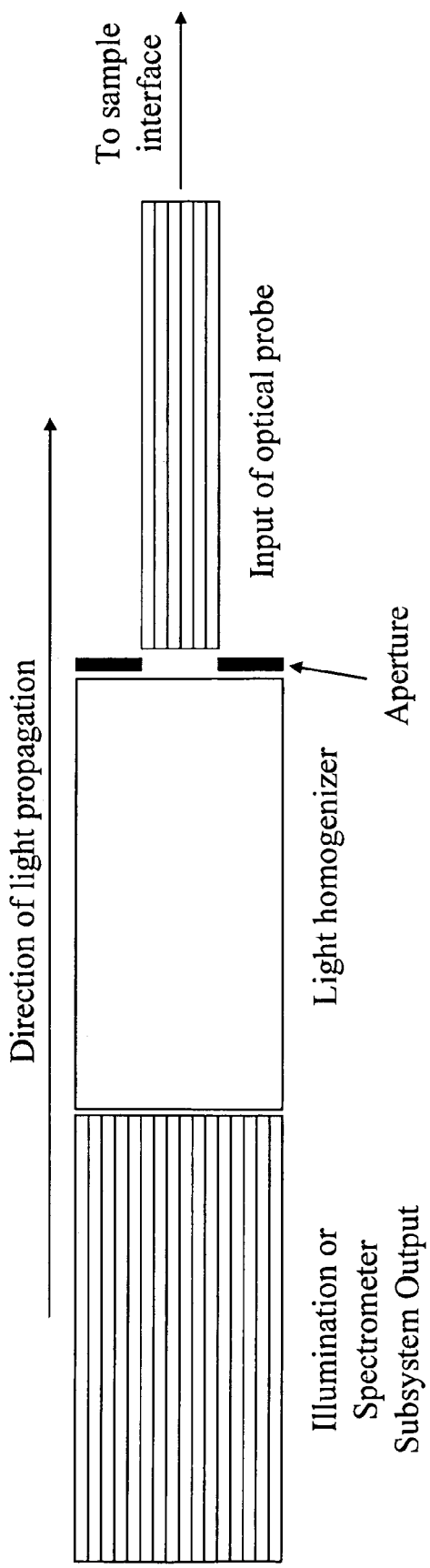
FIG. 6 is a diagram of an arrangement for coupling an illumination or spectrometer subsystem to an optical probe input of dissimilar size using a light homogenizer and aperture.

In embodiments where the physical sizes of the light source or illumination subsystem (100), or spectrometer subsystem (300) are not consistent with the size of the optical probe input, a light homogenizer, such as a light pipe, can be inserted in order to couple the illumination subsystem to the optical probe by spatially and angularly homogenizing the light and provide a better match between the subsystems. In some embodiments, an aperture can be used in conjunction with, or in place or, the homogenizer. FIG. 6 shows a diagram of a coupling arrangement. In addition to, or in place of, a homogenizer or aperture, coupling optics can also be used to match the spatial and angular content of the light source or illumination subsystem (100), or spectrometer subsystem (300) to the input of the optical probe. Suitable examples of coupling optics include, but are not limited to, one or more lenses, mirrors, diffusers, light pipes, optical fibers, or combinations thereof.

Input Angular and Spatial Homogenization

While the above coupling optics are intended to provide a suitable interface between the illumination subsystem (100) or spectrometer subsystem (300) and the optical probe, another aspect of the present invention is to provide spatially and angularly homogenous light at the sample interface for all wavelengths of interest. Light homogenizers are well suited to this purpose, as disclosed in U.S. Pat. No. 6,684,099 to Ridder et al., which is incorporated by reference, and may be used in embodiments where the optical probe input has substantially the same or different area than the light source or illumination subsystem (100), or spectrometer subsystem (300).

Optical Probe Sample Interface

Figure 7:
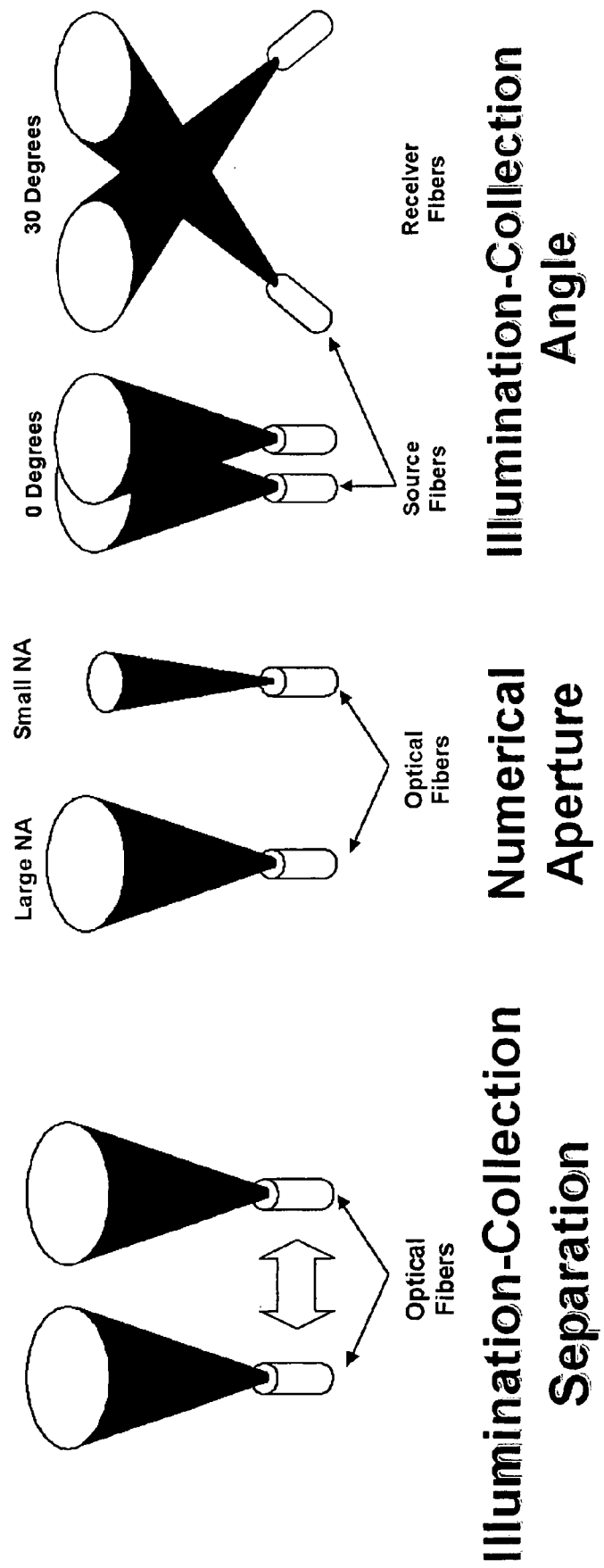
FIG. 7 is a diagram showing the parameters that form a sample interface orientation.

For the purposes of discussing the properties of the sample interface the optical fibers that deliver light from the optical probe input to the sample interface will be referred to as "illumination" fibers. Fibers that deliver light from the sample interface to the output of the optical probe will be referred to as "collection" fibers. The sample interface has multiple properties, including but not limited to its overall size and geometry, the quality of the surface finish, and the configuration of the illumination fibers and the collection fibers. An orientation is comprised of the angle of the illumination fiber or fibers, the angle of the collection fiber or fibers, the numerical aperture of the illumination fiber or fibers, the numerical aperture of the collection fiber or fibers, and the separation distance between the illumination and collection fiber or fibers. FIG. 7 is a diagram of the parameters that form an orientation. One skilled in the art recognizes the wide variety of possible configurations.

Important Properties of the Optical Probe Designs of the Present Invention

Perpendicular Illumination and Collection Fibers

The present invention discloses a family of optical probes that share several common properties at the sample interface that, when combined, offer significant commercial advantages to probes known in the art. First, the angle of both the illumination and collection fibers is zero (e.g., perpendicular to the sample surface). The inventors believe that the perpendicular nature of the fibers to the surface of the sample interface is essential in an optical probe design intended for high volume manufacturing because a highly polished, flat surface is important in non-invasive measurements as it promotes a good interface between the optical probe and the sample. Furthermore, a smooth surface also does not have voids or edges that would be susceptible to contamination from interferents (e.g., dirt or grease).

The perpendicular orientation of the illumination and collection fibers in the present invention allows the sample interface to be ground and polished until it is free of substantial voids, scratches, bumps, or other undesirable features without altering the separation distance between the illumination and collection fibers. In contrast, if either the illumination or collection fibers (or both) are not perpendicular to the sample interface, grinding and polishing becomes a critical and time consuming operation as the separation between the illumination and collection are dependent on how much material is removed during polishing. For example, if too little material is removed the separation will be smaller than desired. While this can be remedied by measurement and removal of additional material, this remedy can be time consuming and expensive. Of larger concern, if too much material is removed, the separation between illumination and collection fibers will be too large. As replacing the removed material is not possible, this often results in an optical probe that does not meet the target specifications and must therefore be rejected. This rejection is a costly result that the family of designs of the present invention avoids. The fabrication process allows for grinding and polishing until sufficient surface quality is obtained without having to be concerned with how much material has been removed. The susceptibility to contamination and manufacturing reproducibility are both critical aspects of commercial feasibility that are not considered in optical probe designs known in the art. This advantage additionally allows for the maintenance and repair of optical probes that have been damaged or contaminated in practical usage, in that they can be re-polished and restored to original condition and specification without the concern of upsetting the spatial relationships in probes with non-perpendicular fibers.

Figure 8:
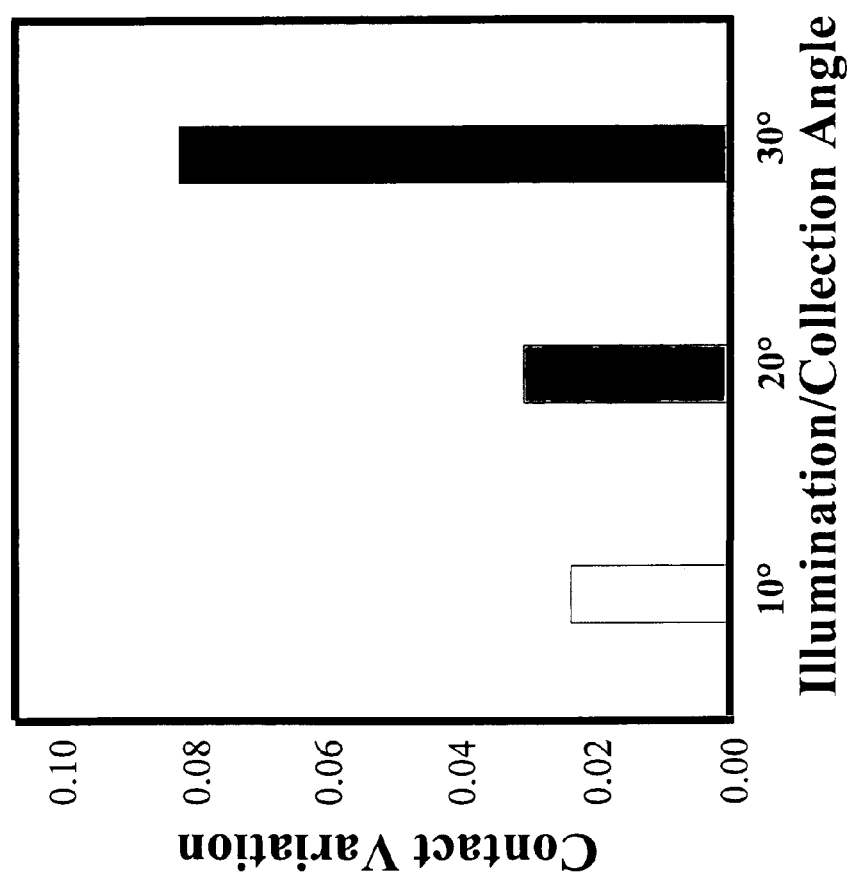
FIG. 8 is a bar chart demonstrating the effect of illumination and collection angle on quality of the interface between the optical probe and sample.

The perpendicular nature of the illumination and collection fibers in the family of optical probes offers advantages in terms of forming a quality interface between the sample and optical probe. This is particularly important when measuring heterogeneous samples, such as human skin, as wrinkles and hair may be present depending on the site of the measurement. FIG. 8 shows the amount of contact variation in spectroscopic measurements of forearm skin tissue for optical probes with varying illumination and collection angles which indicates an increase in the variation as the angle is increased from zero (perpendicular). Contact variation is disadvantageous as it can prevent some individuals (e.g., those with excessive wrinkles) from being measured. Consequently, an advantage of the present invention is the reduction of contact variation that correspondingly reduces the number of individuals that might encounter contact difficulties.

Figure 9:
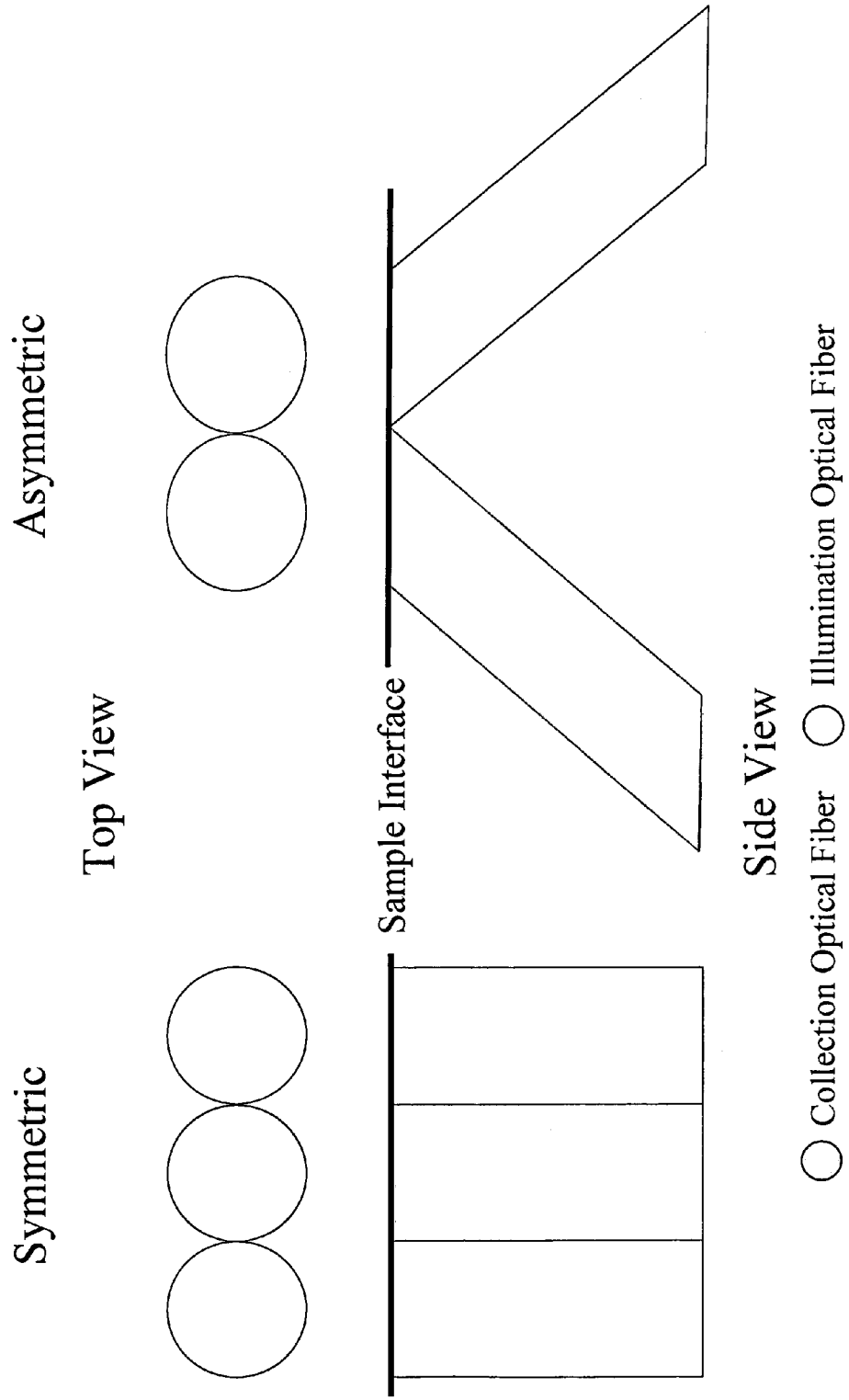
FIG. 9 is a comparison at the sample interface of a symmetric and perpendicular optical probe to an optical probe with no symmetry.

Another important aspect of the perpendicular illumination and collection fibers is that the center of symmetry about each collection fiber is preserved, thereby allowing each to be surrounded by multiple illumination fibers that are geometrically equivalent. As the spectrometer subsystem often has a smaller area of acceptance (e.g., it can be the limiting aperture of the system) an overall efficiency improvement can be realized by using a larger number of illumination fibers and a smaller number of collection fibers. FIG. 9 shows a comparison of a symmetrical and perpendicular optical probe design to an angled design with no symmetry.

Stacks of Linear Rows

The family of optical probe designs of the present invention are each comprised of multiple linear rows. The number of fibers within a row depends on the overall geometry of the probe. For example, an optical probe whose sampling interface is a 200×100 rectangle of optical fibers can be considered in terms of 200 rows of 100 fibers or 100 rows of 200 fibers. On skilled in the art recognizes that designs with multiple columns or diagonals are substantially equivalent to those with multiple rows. Considering the overall design as a stack of linear rows allows a "ribbon" of fibers to be constructed. In one of the examples above, the ribbon would be comprised of 200 fibers. This ribbon can be fabricated such that it is long enough to subsequently be sliced into 100 pieces. These pieces would then be stacked to form the 200×100 arrangement of fibers.

The advantage of this approach is that each of the 100 pieces can be fabricated using the same process and the optical fibers and can be individually checked for broken or dead fibers, misaligned fibers, or other defects that would be difficult to identify in the final assembly. Any of the pieces determined to be defective can be discarded or reworked prior to incorporation into the stack. Probe designs known in the art generally do not make subassembly level quality control checks and are thus only verified at the final assembly. The material cost of rejection of these known probes is higher since the various causes of rejection cannot be caught as early in the manufacturing process.

Another advantage of the stack of ribbons approach is it greatly reduces the handling of individual optical fibers (which are often 200 microns or smaller in diameter) which requires highly trained manual labor. The ribbon formation can largely be automated which results in larger, more robust parts that are easier to handle and less susceptible to breakage. Furthermore, depending on the relationship between illumination and collection fibers in the final assembly, the stacks of ribbons approach is amenable to separating the illumination and collection fibers from each other during the surface interface assembly process rather than after its completion. Some probe designs known in the art require the illumination and collection fibers to be manually identified and separated after the sample interface is fabricated. In contrast, the stack of ribbons approach of the present invention can result in a significant time and cost savings for optical probes in mass production.

Figure 10:
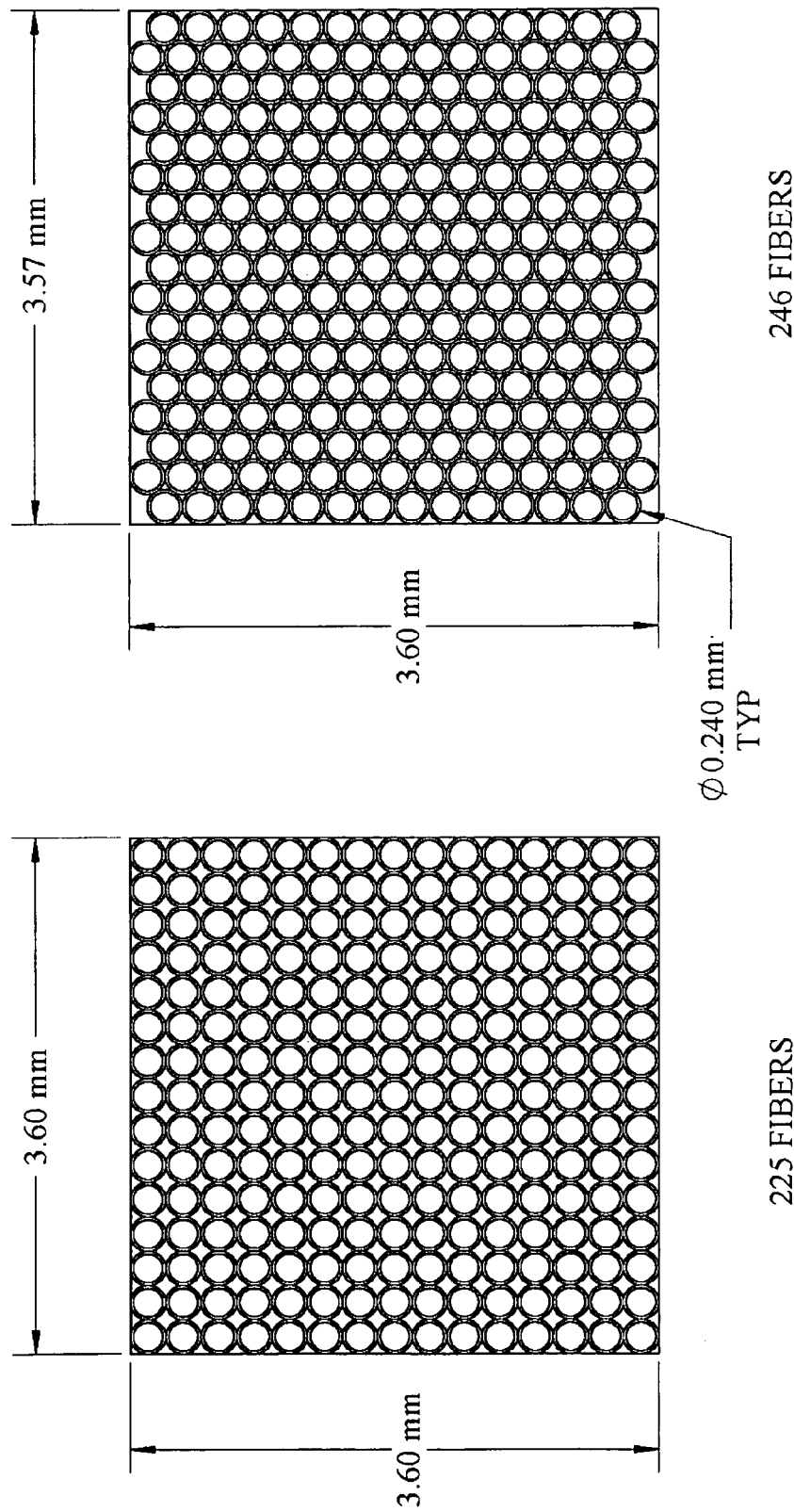
FIG. 10 is a comparison of stack of linear rows and hexpack configurations of optical fibers.

It is recognized in the art that for a fixed sample interface area, optical fibers arranged in a hex-pack configuration result in a higher light throughput than a stack of linear rows when all other design parameters are equal. This is because a hex-pack allows a larger number of fibers to be incorporated into that area. FIG. 10 shows a diagram comparing a stack of linear rows (left) and hex-pack (right). While the added light throughput of the hex-pack can be advantageous, many of the fabrication advantages of the present invention are lost with the hex-pack due to the difficulties in fabricating ribbons that retain the ability to form a hex-pack.

Each ribbon is a linear row of optical fibers that must be mechanically held in proper orientation and alignment. Typically, an adhesive (such as epoxy) is used to form the bond between adjacent fibers. The adhesive must bond to a sufficient surface area or each fiber in order for the bond to be robust. This can result in ribbons where adhesive is present in the physical space where a fiber from another ribbon would ideally reside in a hex-pack configuration. As a result, the fibers in most hex-pack configurations are manually arranged into their final form and then bonded as a complete unit rather than individual rows. Thus, the advantage of the ribbon subassemblies is lost when fabricating a hex-pack configuration in this manner.

Sample Interface Geometry

Figure 11:
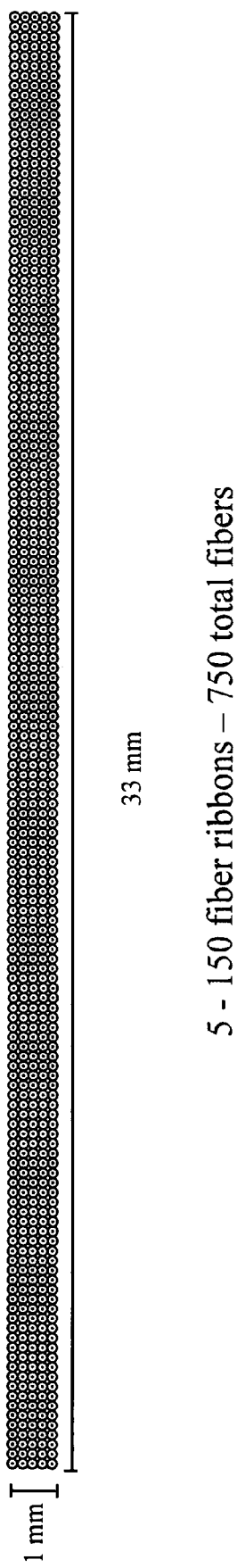
FIG. 11 is a diagram of a rectangular sample interface suitable for a forearm measurement.
Figure 12:
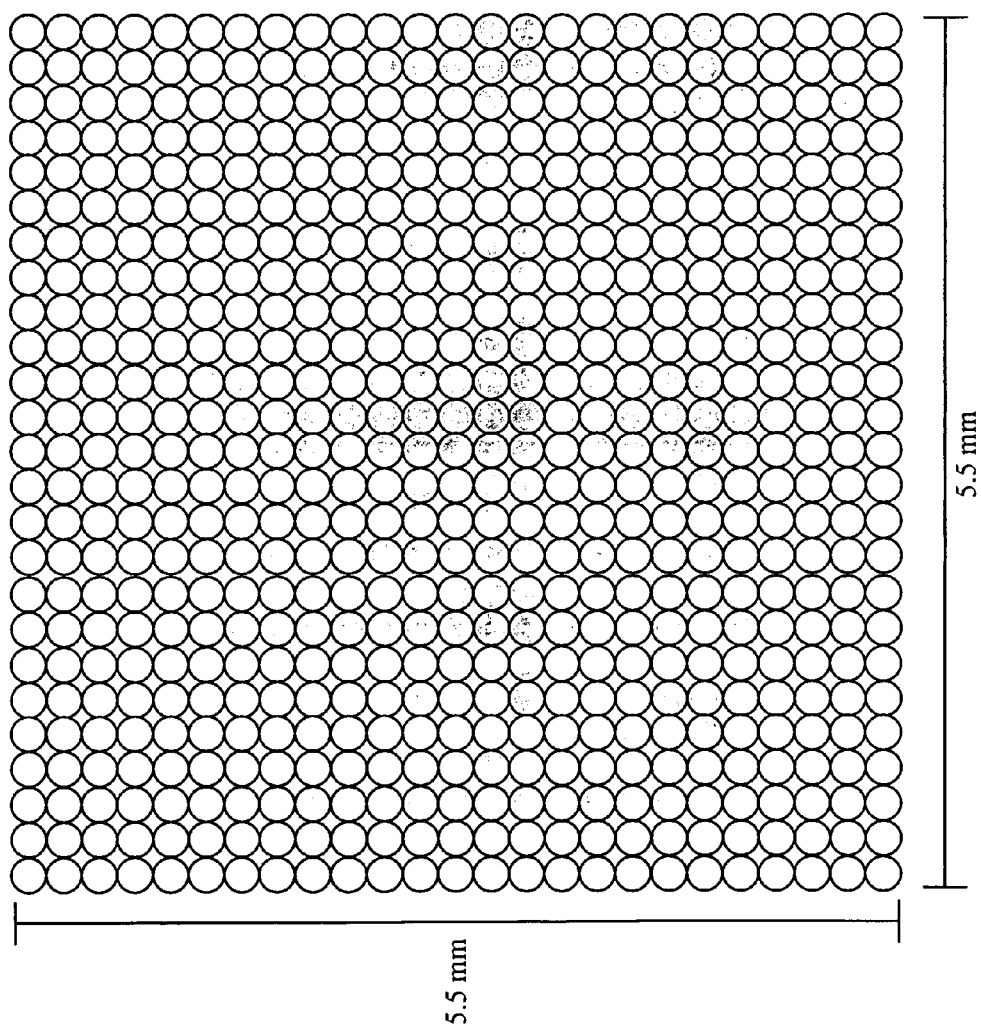
FIG. 12 is a diagram of a sample interface suitable for a smaller measurement site, such as a finger.

The geometry of the sample interface can depend on the physical size and shape of the sample to be measured. For example, an optical probe designed to measure the forearm of a person might be rectangular such that the long axis of the rectangle is oriented with the forearm (FIG. 11). However, some rectangles suitable for forearm measurements might be too large to interface with smaller sites, such as the finger. In these cases, a smaller overall geometry, such as a square, might be more suitable (FIG. 12).

Figure 13:
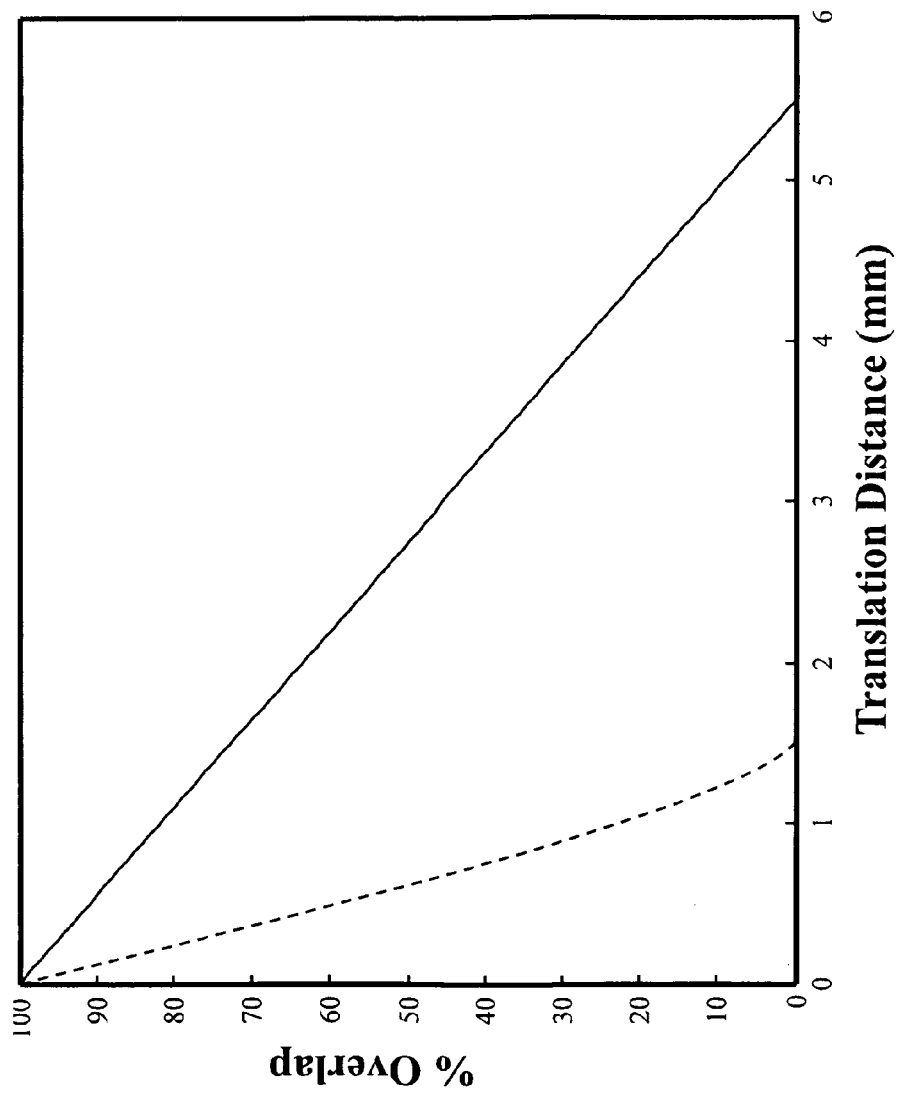
FIG. 13 is a comparison of the area of overlap as a function of translation distance for a continuous area probe (solid line) and a probe comprising separate clusters (dashed line).

In addition, the geometry of the sample interface can be designed to average over a certain area of the sample in order to reduce errors due to sample heterogeneity. In contrast to the known design shown in FIG. 4, that has 6 separate clusters, all of the optical designs of the present invention provide a continuous geometric area that interfaces with the sample. The continuity of the area is an important advantage of the present invention because it improves measurement reproducibility and reduces measurement error. This advantage is because there is always some repositioning error when removing and replacing the sample on the optical probe. FIG. 13 shows that, for a given amount of repositioning error, a continuous area probe design will have an improved area of overlap between sample placements on the optical probe. This continuity of area is especially advantageous because many applications of non-invasive measurements are in unsupervised environments. Consequently, little or no direction may be available to provide aid to the person being measured. As such, any optical probe design that reduces the sensitivity of the measurement to sample placement is advantageous, since the overall robustness of the device is improved.

Spatial Relationship Between Illumination and Collection Fibers

Figure 14:
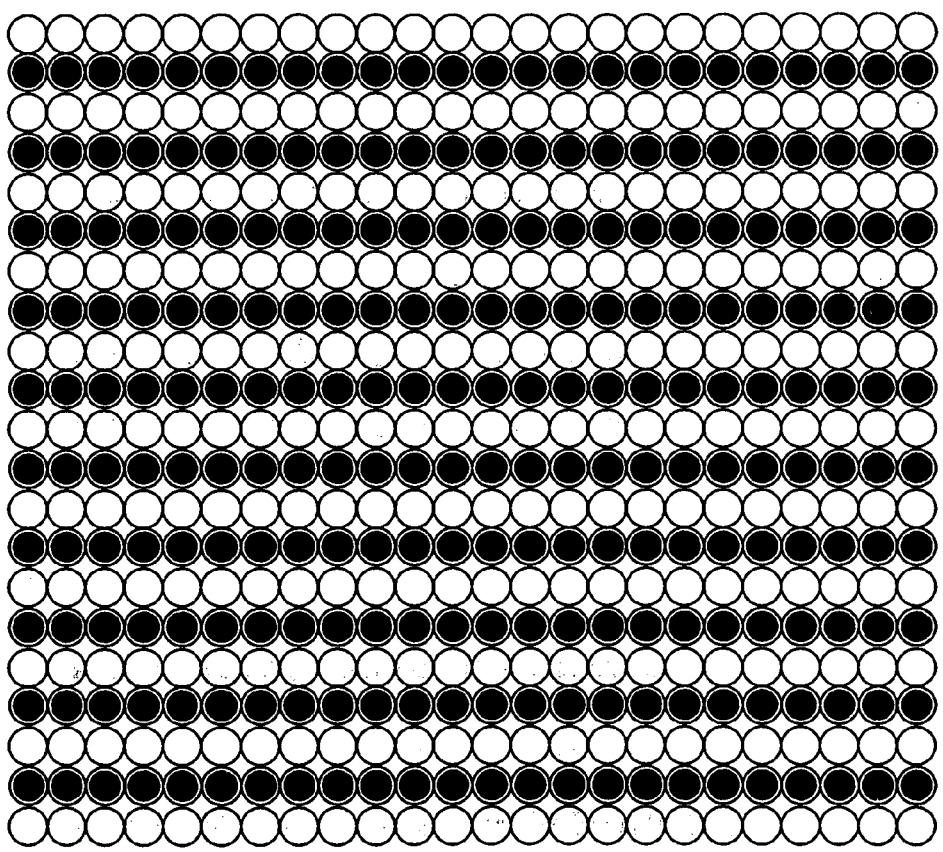
FIG. 14 is a diagram of the sample interface of a linear stack optical probe comprising ribbons of illumination and collection fibers that alternate column-wise.

The following figures and description are intended to describe a few, illustrative relationships between illumination and collection fibers and are not intended to be limiting. Furthermore, each of the illustrated relationships is generally scalable such that it can accommodate any desired sample interface size. For example, FIG. 14 shows a relationship between illumination and collection fibers where the illumination and collection fibers are ribbons that alternate column wise (referred to as a "linear stack"). In terms of scalability, the total size of the sample interface can be adjusted to the target size by increasing the number of fibers in each ribbon (column), or by adding additional ribbons. An advantage of the linear stack is that when each ribbon corresponds to a column, the illumination and collection fibers are easily separated into the input and output of the optical probe.

Figure 15:
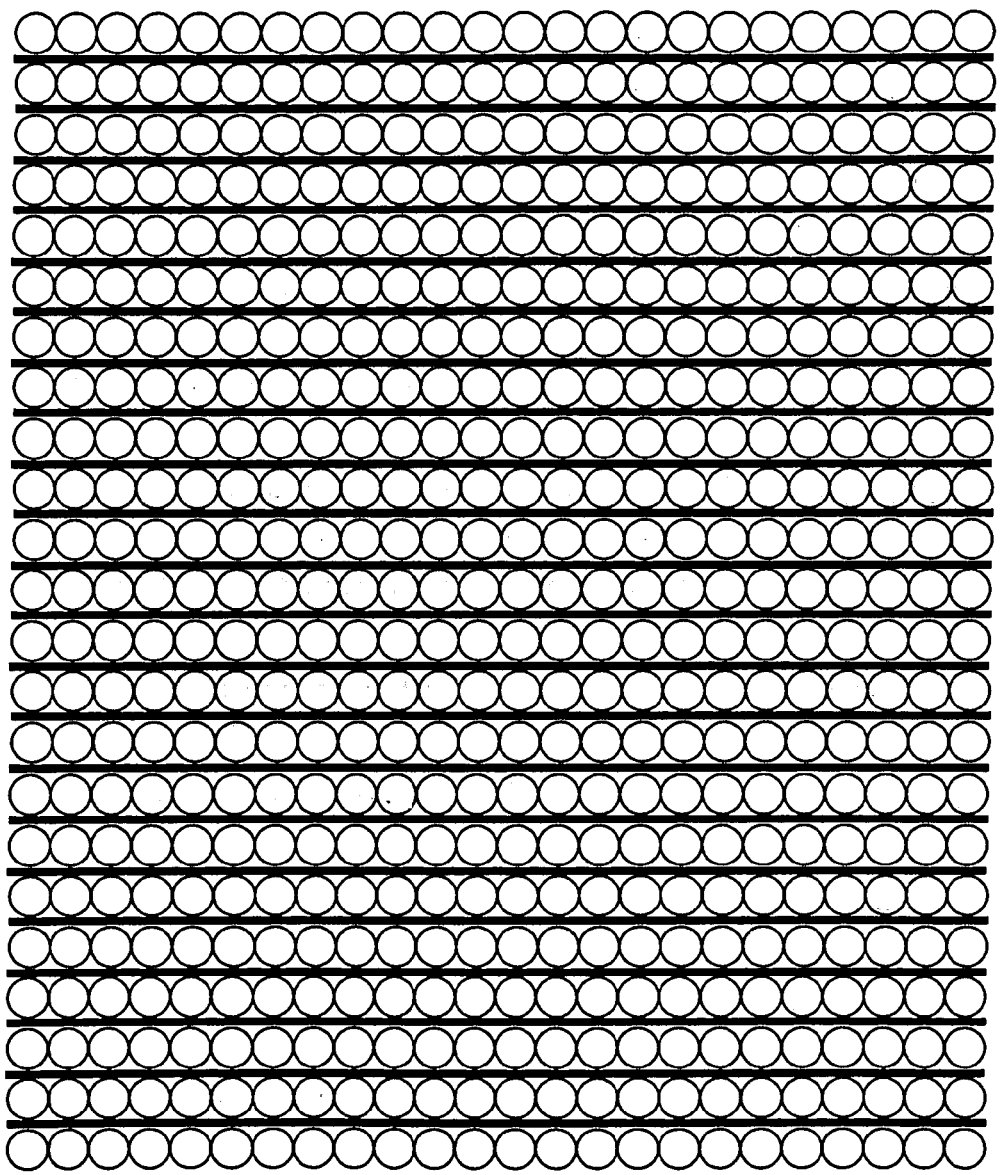
FIG. 15 is a diagram of the sample interface of a linear stack optical probe with spacers between the illumination and collection ribbons.

FIG. 15 shows a variant of the linear stack relationship that incorporates spacers between the illumination and collection ribbons in order to increase their separation. The thickness of the gap can depend on the application of interest and the numerical aperture of the fibers employed, but is generally incorporated into an optical probe design to reject unwanted light and aid in targeting a specific depth in the sample. Depth targeting and light rejection are discussed in further detail later in this disclosure. The spacers can be physical objects, such as metal, glass, or plastic shims, or a distance that is determined during the fabrication process using adhesives.

Figure 16:
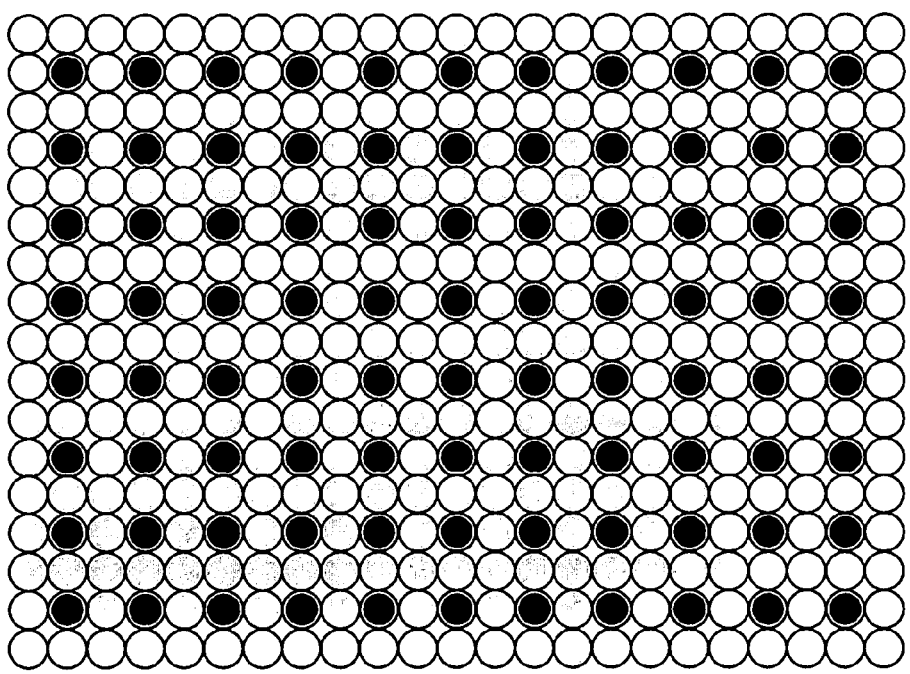
FIG. 16 is a diagram of the sample interface of a linear stack 8:1 optical probe wherein each collection fiber is surrounded by eight illumination fibers.

FIG. 16 shows a variant of the linear stack relationship where the ribbons (columns) of the linear stack comprised of collection fibers are altered such that every other fiber is instead an illumination fiber. The final result is an illumination/collection relationship where each collection fiber is surrounded by eight illumination fibers (referred to as the "linear stack 8:1"). An example of a situation where an illumination/collection relationship of this type is advantageous is when the output area of the illumination subsystem is larger than the input area of the spectrometer subsystem. In this case, a larger number of illumination fibers consistent with the area of the illumination subsystem deliver light to the sample and a smaller number of fibers consistent with the area of the spectrometer subsystem collect light from the tissue. One skilled in the art recognizes that ratios other than 8:1 are possible and are equally suitable for the present invention. Furthermore, the present invention contemplates that the illumination and collection fibers can be reversed for a given relationship (e.g., an 8:1 ratio can just as easily be 1:8).

Figure 17:
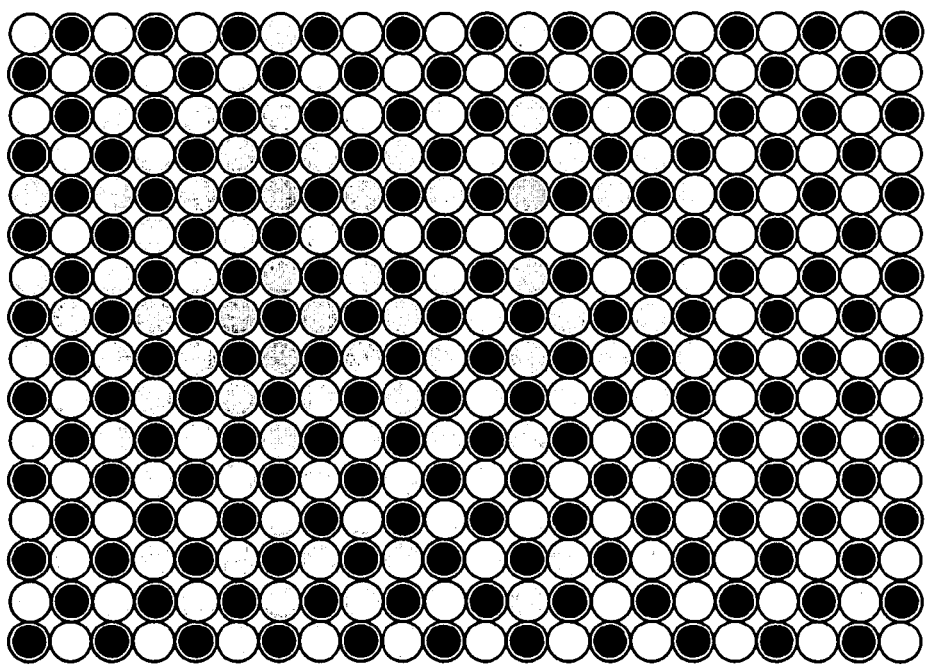
FIG. 17 is a diagram of the sample interface of an alternating linear stack optical probe wherein each collection fiber is surrounded by four illumination fibers.

Another embodiment of the illumination/collection relationship is shown in FIG. 17 which shows that each ribbon (whether considered column-wise or row-wise) is comprised of alternating illumination and collection fibers and is referred to as the "alternating linear stack". An advantage of this embodiment is that each ribbon is essentially equivalent to all others except that every other row is flipped 180 degrees. Consequently, all ribbons can be fabricated using the same process and illumination and collection fibers can be separated prior to combining the ribbons. A further advantage of the alternating linear stack is that while the ratio of illumination to collection fibers is 1:1 similar to the linear stack, each collection fiber has 4 adjacent illumination fibers while the linear stack has 2. Consequently, an efficiency improvement of the alternating linear stack relative to the linear stack is achieved.

Figure 18:
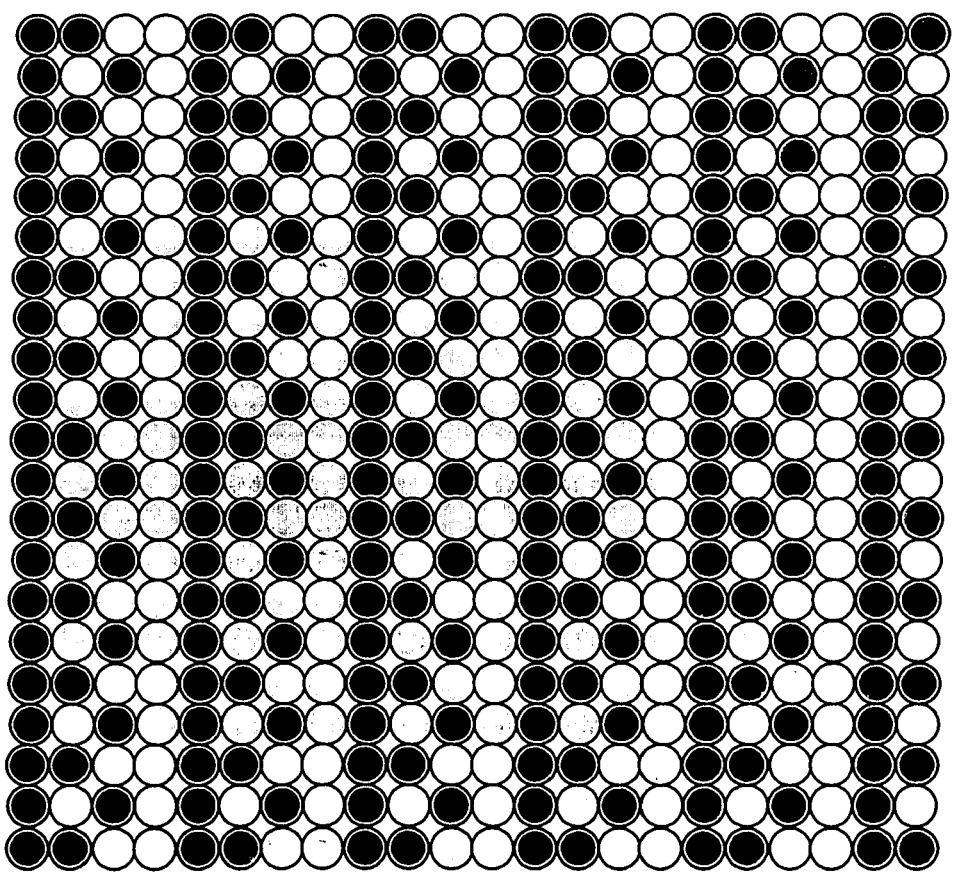
FIG. 18 is a diagram of the sample interface of an alternative embodiment that can be used with a multi-channel optical probe.

The illumination/collection relationships disclosed above can be combined and extended to generate a large number of permutations. FIG. 18 shows an embodiment of such an extension that combines multiple ribbons, all of the same length. However, some ribbons are comprised solely of illumination or collection fibers, while others alternate. These relationships can be useful in some applications and embodiments, including but not limited to those that incorporate multi-channel optical probes (discussed in additional detail later in the disclosure). Furthermore, while FIGS. 17 and 18 show the fibers alternating in a 1:1 pattern, other patterns such as 1:2 or 2:2 are possible and contemplated in the present invention. One skilled in the art recognizes the wide range of permutations of illumination and collection relationships, sample interface geometries, and sample interface sizes, contemplated in the present invention.

Optical Probe Output

The output of the optical probe is comprised of the collection fibers. The number of collection fibers can depend on the overall geometry and illumination/collection pattern at the sample interface, the size of the input aperture of the spectrometer subsystem (300) or data acquisition subsystem (400). The geometry of the optical probe output can be circular, rectangular, or a linear slit, depending on the input acceptance of the spectrometer subsystem (300) or data acquisition subsystem (400). For example, if a dispersive (e.g., grating) spectrometer subsystem (300) with an input slit is employed, a linear or rectangular arrangement of optical fibers would be desirable for the output of the optical probe such that it efficiently interfaces with the input slit of the spectrometer.

In many cases, the sample under consideration (e.g., skin tissue) can be spatially heterogeneous in terms of its optical and chemical properties. This heterogeneity can result in each collection fiber at the sample interface collecting light with different spatial, angular, and chemical information. As the output of all spectrometers, whether dispersive or modulating, is sensitive to angular and spatial content in addition to light intensity as a function of wavenumber, it is advantageous to homogenize the output of the collection fibers prior to introduction to the spectrometer subsystem (300), or in some embodiments the data acquisition subsystem (400). The homogenization results in the output of each collection fiber being mixed with the outputs of the other collection fibers such that they all contribute substantially equally to the light introduced to the spectrometer subsystem (300) or data acquisition subsystem (400). Light homogenizers, such as those described in incorporated U.S. Pat. No. 6,684,099 to Ridder et al., are well suited to this purpose.

Figure 19:
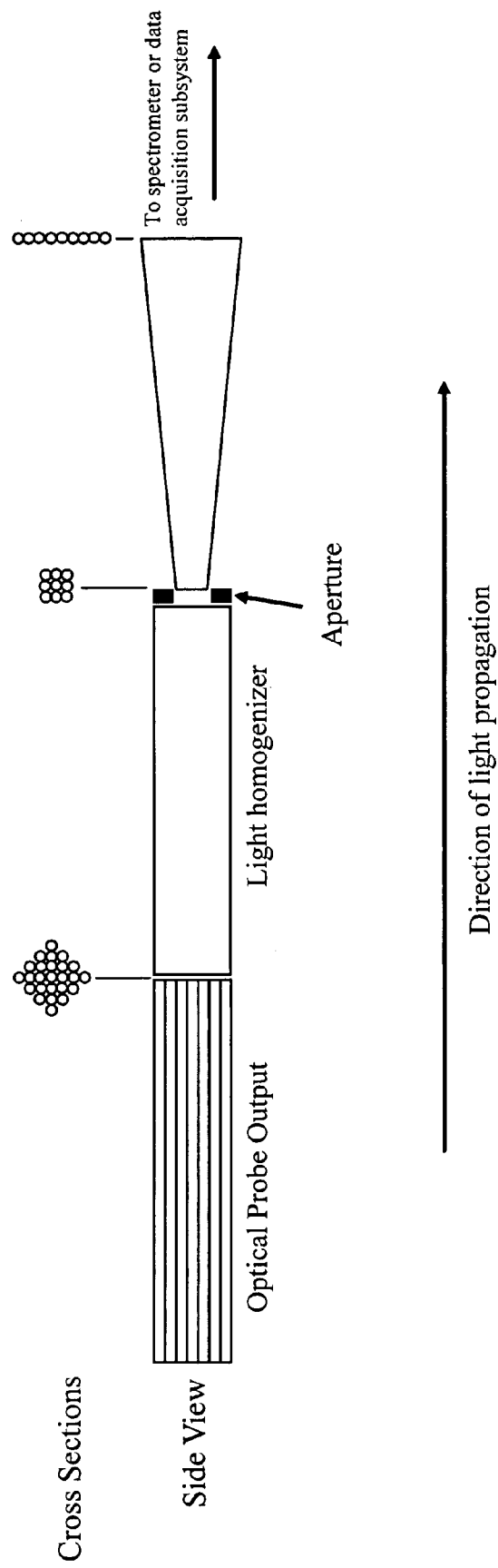
FIG. 19 is a diagram of an embodiment of an optical probe output showing homogenization of the output of the collection fibers and output geometry conversion.

Another aspect of light homogenizers is the ability to homogenize the collected light prior to converting the shape of the output. FIG. 19 shows an example embodiment where the collection fibers of the optical probe are collected into a circular arrangement and introduced to the input of a hexagonal light pipe in order to spatially homogenize the outputs of the fibers. The output of the light pipe is then introduced to another bundle of optical fibers. The output of this bundle can be of any geometric shape (square, rectangular, linear, etc) such that it interfaces efficiently with the spectrometer subsystem (300) or data acquisition subsystem (400). One skilled in the art recognizes that many variants of this approach exist, including but not limited to, replacing the straight hexagonal light pipe with another homogenizer, such as a bent light pipe, in order to provide angular and spatial homogenizing, and inclusion of an aperture at the output of the homogenizer in order to reduce the size of the output. In embodiments where the number of collection fibers in the optical probe exceeds the number that can be accepted by the spectrometer subsystem (300) or data acquisition subsystem (400), the aperture can be advantageous.

Additional Aspects of the Probe Designs of the Present Invention

Optical Fiber Materials

Figure 20:
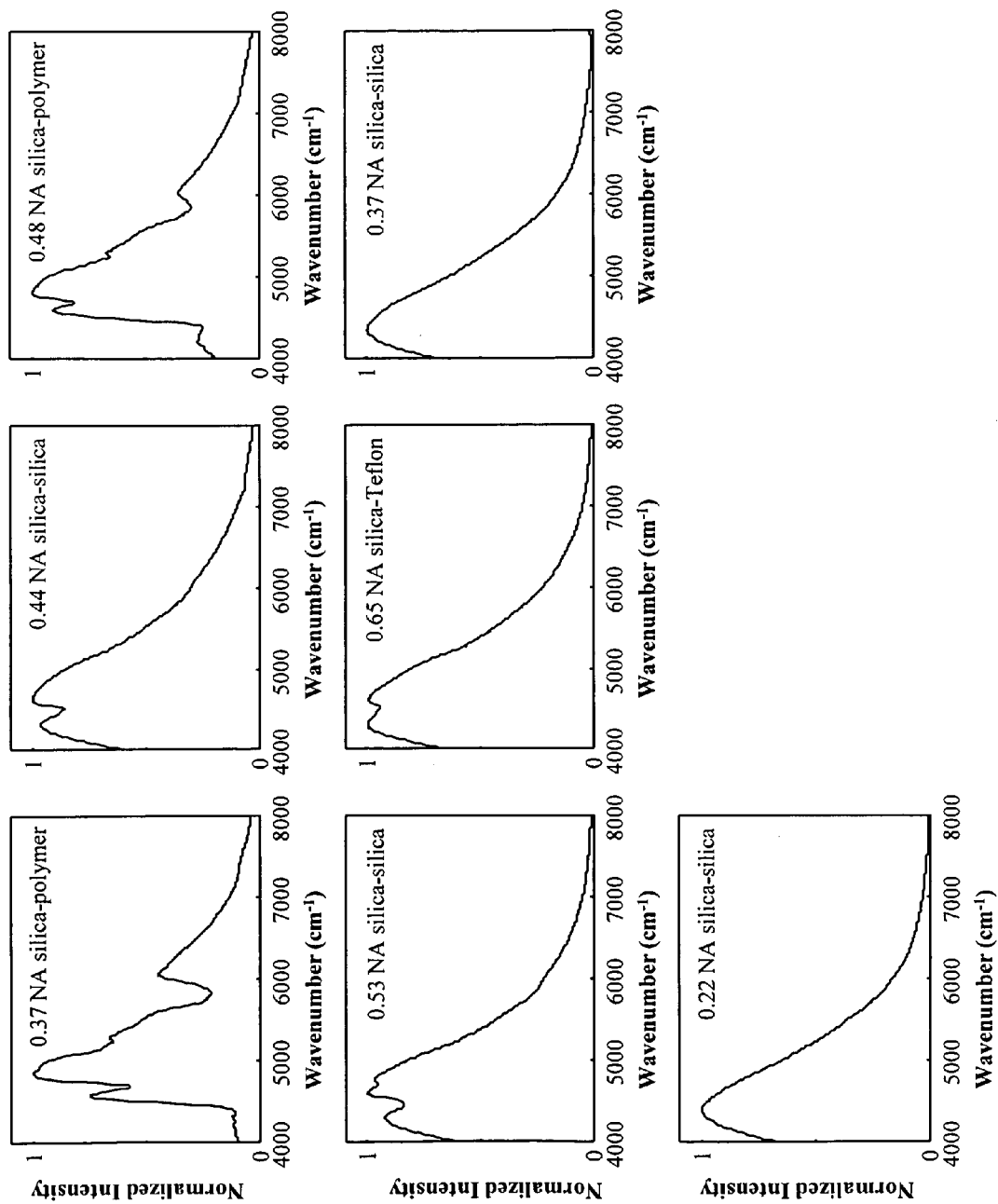
FIG. 20 is a diagram of the near-infrared absorbance spectra of various optical fibers suitable for the present invention.

The selection of a specific type of optical fiber for a given probe design is driven by several properties, including, but not limited to, the numerical aperture, absorption properties, cost, mechanical adhesion properties, physical robustness, and sensitivity to contamination. It is generally desirable, but not required, to select an optical fiber that does not impart absorbance signals due to the materials used in its fabrication. FIG. 20 shows the absorbance spectra of several optical fibers in the near-infrared spectral region that shows varying degrees of absorption for different types of fibers.

Another consideration is the numerical aperture (NA) of the optical fiber. According to equation (1), the numerical aperture of an optical fiber is related to the difference in refractive index of the core and cladding of the fiber.

$$NA = \sqrt{n_1^2 - n_2^2} \tag{1}$$

where $n_1$ is the refractive index of the core and $n_2$ is the refractive index of the cladding of the optical fiber.

As higher NA represents a wider range of illumination or collection angles, the efficiency of the optical probe generally increases as the NA increases. The wider range of angles comes at the expense of a larger number of potential paths for the light to travel through the sample, which can be a drawback in some applications. Another consideration is that large NA's can result in an increase in specular (or short optical path) due to these light rays bouncing off the surface of the sample and being collected without ever entering the sample. This is generally undesirable and can be suppressed by placing a blocker, or spacer, between the illumination and collection fibers such that these short path and specular rays do not travel far enough to be collected.

In some embodiments, more than one type of optical fiber can be used in order to provide better control of light propagation through the sample. For example, the illumination fibers can be comprised of high-NA optical fibers and the collection fibers can be comprised of low-NA fibers. One skilled in the art recognizes that a large number of permutations are possible, including multiple fibers of different NA's in both illumination and collection.

In cases where an optical fiber of a desired NA is unavailable, a higher NA fiber can be used in conjunction with NA reducing optics at the input and output of the optical probe. For example, if 0.4 NA is desired, 0.65 NA Teflon-silica fibers can be used in conjunction with sets of collimating optics and apertures at the input and output of the optical probe to reduce the NA from 0.65 to 0.4.

The mechanical adhesion and other physical properties of the optical fibers are also important to consider. As an example, while Teflon-silica fibers offer a large numerical aperture that can be desirable, the mechanical properties of Teflon can complicate fabrication. Adhesives do not perform well when in contact with Teflon, the Teflon itself is fragile and prone to damage and contamination from liquids. In some embodiments of the present invention, these negative physical properties are offset by its advantageous optical properties, while in others (particularly in high volume applications), the physical properties of Teflon-silica fibers can preclude their use. The Teflon fibers above are one example of optical fibers based on fluoropolymers, one skilled in the art recognizes that optical fibers incorporating other fluoropolymers are available from a variety of sources and are equally suitable for the present invention In many preferred embodiments of the present invention, fused silica core with fused silica cladding (silica/silica) optical fibers can be used. While the most common silica/silica optical fiber is 0.22 NA, several different atoms or combinations of atoms can be doped into one or both of the cladding and core in order to alter the refractive index of the material. Suitable dopants include praseodymium, cadmium, halides, germanium, silicon, aluminum, rare earths, or any other atom or combination of atoms. Several new variants of Si/Si fibers have recently become available that have advantageous properties for non-invasive optical probes. For example, a 0.37 NA silica/silica fiber is available that offers a wider NA than the more commonly available 0.22 NA silica/silica fiber, while imparting virtually no absorbance. Furthermore, as both the core and cladding are fused silica, they are mechanically robust, work well with adhesives, and are difficult to contaminate. These fibers can provide an excellent set of optical and physical properties for many embodiments of the present invention.

Depth Targeting and Path Rejection

Figure 21:
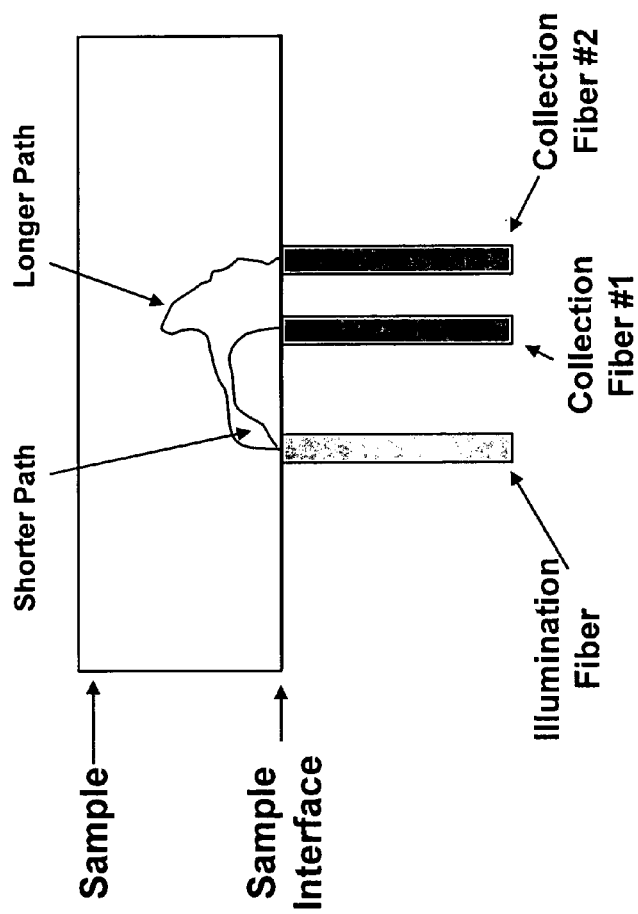
FIG. 21 is a diagram showing the depth and pathlength effects of varying the illumination and collection fiber separation.
Figure 22:
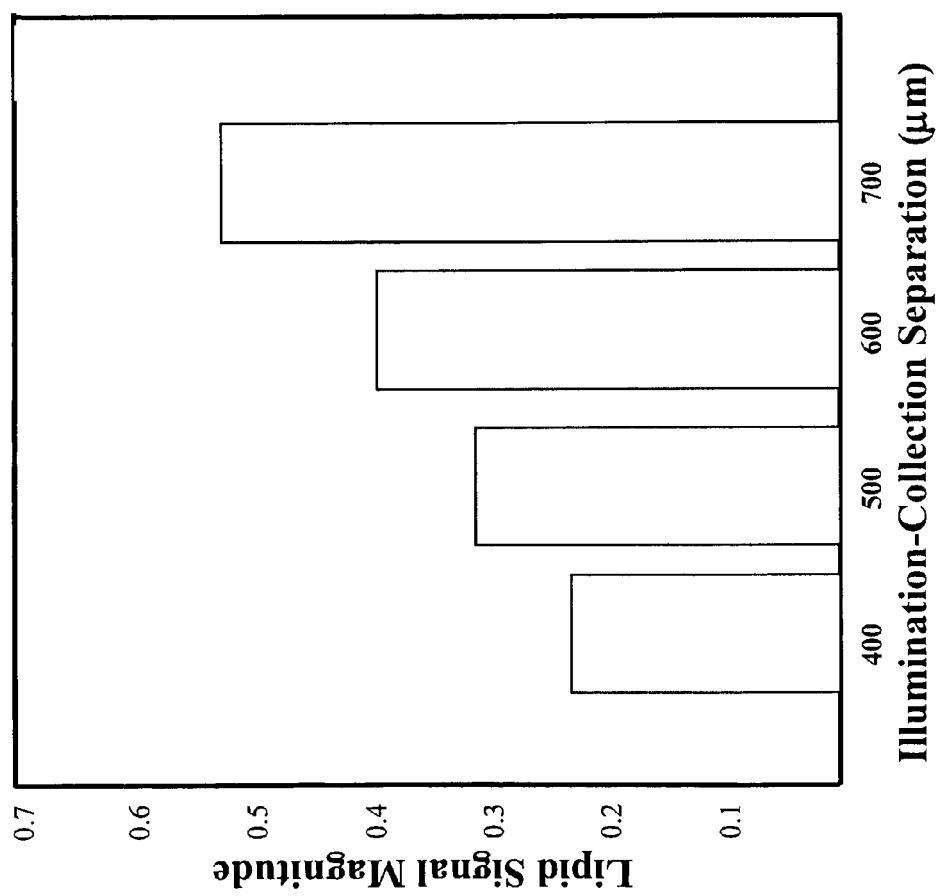
FIG. 22 is a bar chart showing lipid signal content for different illumination and collection fiber separations.

The illumination fibers of the sample interface can, depending on the probe design, illuminate the tissue in a manner that targets the compartments of the tissue pertinent to the attribute of interest, and can discriminate against light that does not travel a significant distance through those compartments. As an example, a 100-μm separation between illumination and collection fibers can be used to discriminate against light that has negligible pathlength through the sample, which consequently contains little attribute information. The tissue sampling interface can reject surface reflections and short pathlength rays and it can collect the portion of the light that travels the desired pathlength through the tissue with high efficiency in order to maximize the net attribute signal of the system. The tissue sampling interface can employ optical fibers to channel the light from the input to the tissue in a predetermined geometry as described above. The optical fibers can be arranged in a pattern that targets certain layers of the tissue that contain good attribute information. The spacing, angle, numerical aperture, and placement of the illumination and collection fibers can be arranged to achieve effective depth targeting. For example, FIG. 21 demonstrates that increasing the separation between the illumination and collection fibers at the sample interface tends to promote longer light pathlengths that penetrate deeper into the sample. FIG. 22 shows the lipid content of skin tissue spectra acquired at multiple illumination and collection fiber separations. Lipids are typically present in the subcutaneous layer of the skin (deeper than the epidermis and dermis), thus increased lipid signal is indicative of deeper penetration into the skin.

Temperature Control and Index Matching

In some embodiments of the present invention, a device that thermostats the sample interface is included such that it assists in controlling the temperature of the sample during the measurement. The temperature of the sample interface is set such that the invention reduces prediction errors due to temperature variation. In some embodiments, an apparatus that repositions the sample on the sample interface in a repetitive fashion is included. In some embodiments, an index matching fluid can be used to improve the optical interface between the sample and sample interface. The improved interface can reduce error and increase the efficiency, thereby improving the measurement. See, e.g., U.S. Pat. No. 6,622,032 to Robinson et al., which is incorporated herein by reference.

Overview of Manufacturing Process

Verification of design parameters and tolerances is critical to ensure performance. Furthermore, as many non-invasive measurements involve humans, they can fall under regulatory compliance agencies such as the FDA. As such, a clear means for verifying conformance of manufactured probes to their respective designs is another advantage of the optical probes disclosed in the present invention.

The designs of the present invention are amenable to high volume manufacturing techniques which allows transferring many manual, labor intensive operations to repetitive tasks using fixtures and other techniques. This has several beneficial effects, including reduced labor for each probe manufactured, reduced manufacturing time, reduced cost, and improved consistency across multiple units of the same design. These are all critical aspects to a commercially viable product.

Figure 23:
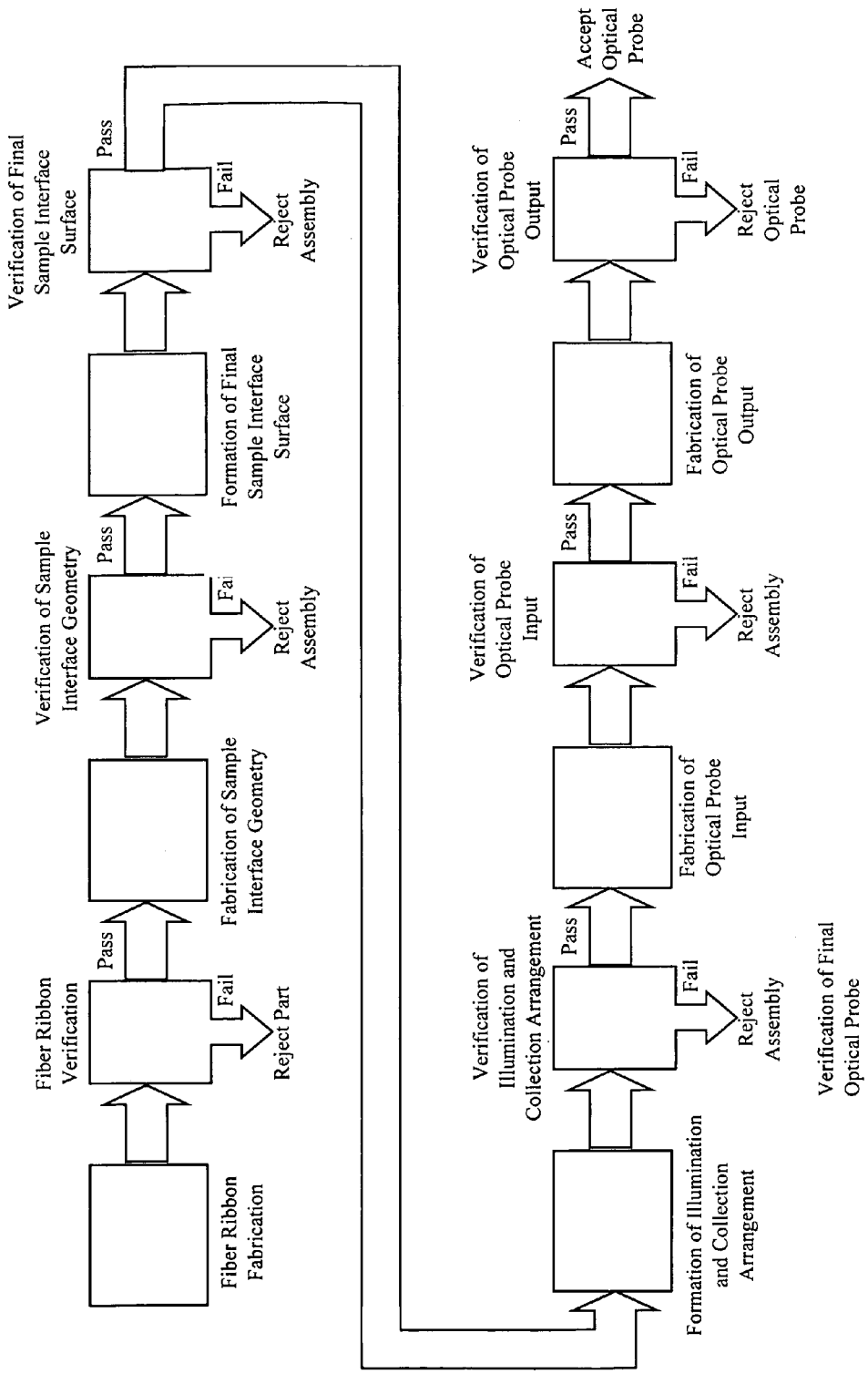
FIG. 23 is a diagram of an optical probe manufacturing and verification process.

Many optical probe designs known in the art involve the alignment of parts with tolerances in the micron regime. Depending upon the number of optical fibers, overall orientation and geometry of the fibers, etc. the process of fabricating a single probe can be time consuming and prone to errors. A major advantage of the present invention is that the optical probe designs are created from subassemblies of optical fibers that can be fabricated and verified prior to incorporation into the final unit. This approach allows each subassembly to be significantly less complex and therefore easier to fabricate. Furthermore, the completed subassemblies can be verified to be in conformance with design tolerances prior to incorporation into the final assembly. Any failed subassemblies can be identified at that point and either scrapped or reworked. Failures in the fabrication of known optical probe designs are typically identified in the final assembly, which is costly in both time and money. A schematic diagram of a suitable manufacturing and verification process for the optical probe of the present invention is shown in FIG. 23. For demonstrative purposes, the steps depicted in FIG. 23 are discussed in further detail below.

Fiber Ribbon Fabrication

The first step in the manufacturing process is the fabrication of the optical fiber ribbons that will be subsequently stacked to form the desired sample interface geometry. The number of fibers for a given ribbon can be determined based on either the lesser or greater of the dimensions of the desired sample interface geometry. In either case, the objective is to form a linear row of fibers that comprise a ribbon. The tolerances on the linearity can depend on the application of interest and the fabrication technique used to form the ribbon. In some embodiments of the present invention, the fibers to be incorporated into the ribbon can be held in position via a mechanical fixture or clamp and subsequently fixed in place using an adhesive. The adhesive can be epoxy or any other suitable adhesive that results in the desired mechanical and environmental stability.

Fiber Ribbon Verification

Following its fabrication, the relevant parameters of a ribbon are then verified in order to determine its suitability for inclusion in an optical probe assembly. Any ribbon that is determined to have failed the verification step can be discarded, re-worked, or used in a different optical probe design where the ribbon meets the respective requirements. Some examples of parameters that are typically verified include, but are not limited to, the presence of adhesive in undesirable locations (e.g., on outer edges of the ribbon), the number of broken or poorly transmitting fibers, and the proper length of the ribbon.

Fabrication of Sample Interface Geometry

The next step in fabricating an optical probe is to form the desired sample interface geometry. This is accomplished by stacking ribbons, each of which has passed its respective verification step. The stacking procedure can be iterative (e.g., adding one or more ribbons at a time in multiple steps) or a single step (all ribbons are combined at once). In either case, the stacked ribbons can then be coarsely polished in order to provide a surface for the subsequent verification step. As with the ribbon fabrication, the adhesive can be epoxy or any other suitable adhesive that results in the desired mechanical and environmental stability.

The stack of ribbons can also be incorporated into a mechanical fixture or similar assembly. This assembly can serve multiple purposes including, but not limited to, holding the sample interface at a fixed position relative to the optical probe input and output and providing a larger surface at the sample interface in order to provide better support for a large sample like the forearm.

Verification of Sample Interface Geometry

Following its fabrication, the stack of ribbons is verified in order to determine if it is suitable to proceed to the next step. Any stack of ribbons that is determined to have failed the verification step can be discarded, re-worked, or potentially used in a different optical probe design where the stack of ribbons meets the respective requirements. Some examples of parameters that are typically verified include, but are not limited to, the alignment of fibers across the ribbons in the stack, the presence of adhesive in undesirable locations, the number of broken or poorly transmitting fibers, and the overall size and geometry of the stack of ribbons at the sample interface.

Formation of Final Sample Interface Surface

The next step in the manufacturing process is to form the final sample interface via polishing the surface to the desired flatness, smoothness, and overall surface quality. In some embodiments, this step can be combined with the previous step. The final polish can be time consuming or labor intensive. As a result, it is disadvantageous to polish assemblies that would fail verification for other reasons. In these cases, it is advantageous to keep the final polish as a separate step.

Verification of Final Sample Interface Surface

Following the final polish, the assembly is verified in order to determine if it is suitable to proceed to the next step. Any assembly that is determined to have failed the verification step can be discarded, re-worked, or potentially used in a different optical probe design where the assembly meets the respective requirements. Some examples of parameters that are typically verified include, but are not limited to, the flatness of the surface, the number and size of defects (e.g., voids and scratches) in the surface, the overall smoothness of the surface, and the number of broken or poorly transmitting fibers.

Formation of Illumination and Collection Arrangement

Once the surface finish of the sample interface has been verified, the next step is to separate the fibers into illumination and collection fiber groups depending on the optical probe design's target arrangement. In the case of a linear stack arrangement where all fibers of a given ribbon are either illumination or collection fibers, this step can be combined into the stack fabrication step. In other arrangements, such as a linear stack 8:1, there are both illumination and collection fibers within some (but not necessarily all) ribbons. Therefore, this step involves separating the fibers within those ribbons into their appropriate input (illumination) or output (collection) group.

In some embodiments, the non-sample interface end of a fiber can be illuminated with white or colored light. Assuming that the color of this light is different than the ambient light, the location of the fiber in the pattern of fibers at the sample interface can be determined (e.g., by finding the fiber that corresponds to the non-ambient color). Then, based on the target arrangement of the optical probe design, the fiber can be added to its respective input or output group. In some embodiments, fiber groups, rather than single fibers can be illuminated.

Another approach that can be used to separate fibers into illumination and collection fiber groups is to apply a mask to the sample interface to block all illumination (or equivalently all collection) fibers. A light can then be used to irradiate all unmasked fibers. The unmasked fibers will transmit the light to their respective ends, thus allowing them to be separated from their dark, masked counterparts. A variant of this approach is to design a mask that filters some colors from sample interface locations corresponding to illumination fibers and other colors from areas corresponding to collection fibers. In this case, a white light can be used to illuminate all fibers simultaneously. At the terminating ends of the fibers, the illumination fibers will emit one color and the collection fibers another color, thus allowing their straightforward separation.

Figure 24:
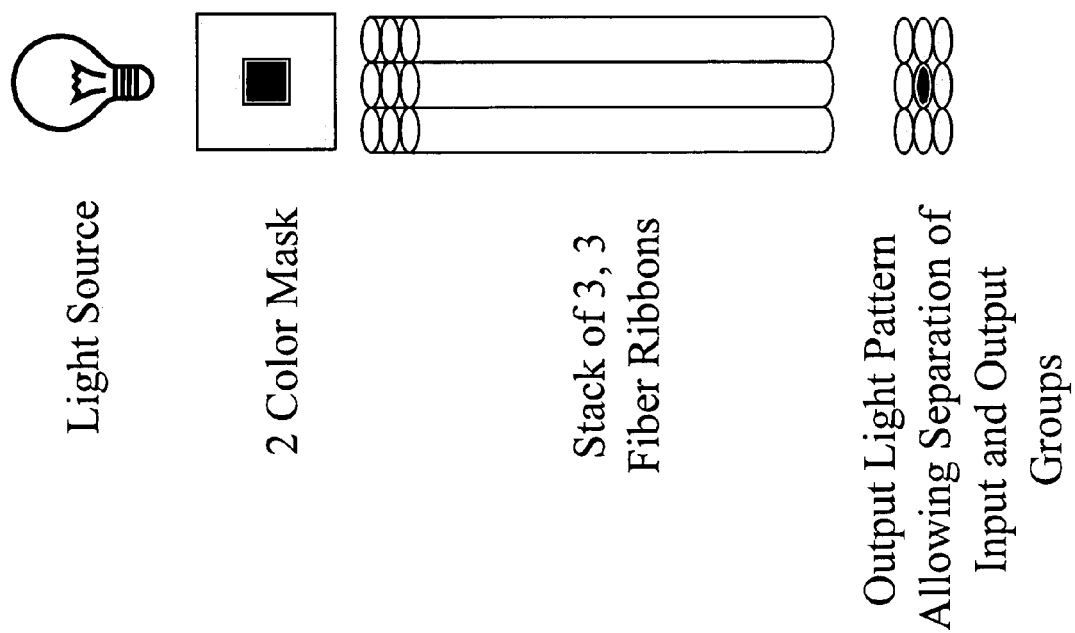
FIG. 24 is a schematic illustration of a fixture allowing visual verification of the separation of optical fibers into illumination (input) and collection (output) fiber groups.

FIG. 24 shows a schematic illustration of this separation process for a simple optical probe design.

Verification of Illumination and Collection Arrangement

Once the optical fibers have been separated into input and output fiber groups, several verification measurements can be performed prior to fabrication of the final optical probe input and output. Any assembly whose input and output fiber groups do not pass the verification measurements can be returned to the separation step, discarded, or potentially used in a different optical probe design where the assembly meets the respective requirements. Some examples of parameters that are typically verified include but are not limited to the number of broken or poorly transmitting fibers, the correct number of input and output fibers, and the correct arrangement of illumination and collection fibers at the sample interface.

The fiber arrangement can be visually or automatically verified by illuminating the terminating ends of the input group of fibers with one color of light and the terminating ends of the output group of fibers with another. One or more color or grayscale images of the sample interface can then be acquired in order to determine if the illumination and collection fibers are properly arranged.

Fabrication of Optical Probe Input

Once the group of input fibers has been identified and verified, they can be inserted into a ferrule consistent with the desired input geometry. For example, if the illumination subsystem has a circular output, the optical probe input could also be a circle of the same diameter. Several geometries are possible within the scope of the present invention and include, but are not limited to, circular, hexagonal, square, rectangular, or linear geometries.

Regardless of the geometry of the optical probe input, the group of input fibers is inserted into the ferrule. The fibers can be held within the ferrule using mechanical pressure or via a suitable adhesive. The end of the input is then ground and polished to provide a consistent and smooth interface to the illumination or spectrometer subsystem depending on the overall system orientation.

Verification of Optical Probe Input

Once the optical probe input has been fabricated, several verification measurements can be performed. Any optical probe whose input does not pass the verification measurements can be reworked, discarded, or potentially used in a different optical probe design where the probe meets the respective requirements. Some examples of parameters that are typically verified include, but are not limited to, the number of broken or poorly transmitting fibers, the flatness of the surface, the number and size of defects (e.g., voids and scratches) in the surface, the overall smoothness of the surface, or contaminants such as adhesive on the ends of the fibers.

Fabrication of Optical Probe Output

Once the group of output fibers has been identified and verified, the can be inserted into a ferrule consistent with the desired output geometry. For example, if the spectrometer or data acquisition subsystem (depending on the system orientation) has a circular input, the optical probe output could be a circle of the same diameter. Several geometries are possible within the scope of the present invention and include, but are not limited to, circular, hexagonal, square, rectangular, or linear geometries.

Regardless of the geometry of the optical probe output, the group of output fibers is inserted into the ferrule. The output fibers can be held within the ferrule using mechanical pressure or via a suitable adhesive. The end of the output is then ground and polished to provide a consistent and smooth interface to the spectrometer or data acquisition subsystem depending on the overall system orientation.

Verification of Optical Probe Output

Once the optical probe output has been fabricated, several verification measurements can be performed. Any optical probe whose output do not pass the verification measurements can be reworked, discarded, or potentially used in a different optical probe design where the probe meets the respective requirements. Some examples of parameters that are typically verified include but are not limited to the number of broken or poorly transmitting fibers, the flatness of the surface, the number and size of defects (e.g., voids and scratches) in the surface, the overall smoothness of the surface, or contaminants such as adhesive on the ends of the fibers.

Final Optical Probe Verification

Once an optical probe has completed the individual fabrication and verification steps, it can be advantageous to perform a final verification step on the completed assembly. Some examples of parameters that can be verified include the illumination and collection arrangement, the surface quality of sample interface, the surface quality of the input, the surface quality of the output, the number of broken or poorly transmitting optical fibers in the input and output, the alignment of the sample interface, the size of the sample interface, and the geometry of the sample interface. These parameters can be verified by the same or different approaches as those described in the individual verification steps.

Multichannel Probe Designs

Figure 25:
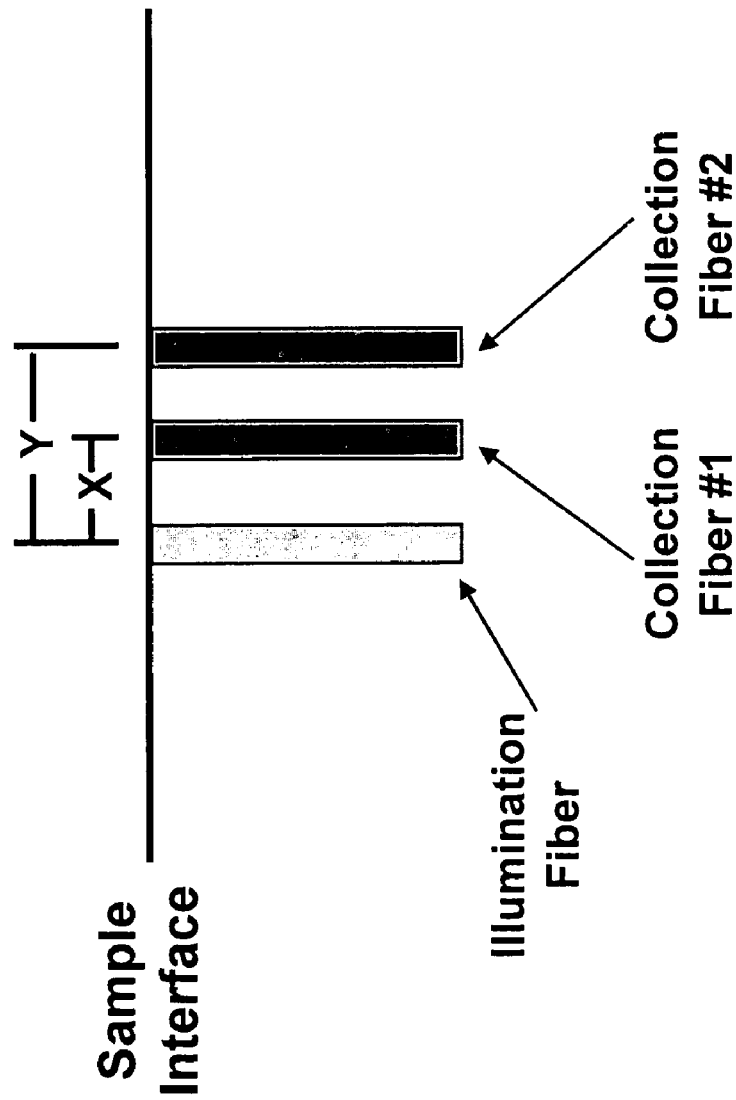
FIG. 25 is a schematic illustration showing a cross-section of a 2 channel optical probe.
Figure 26:
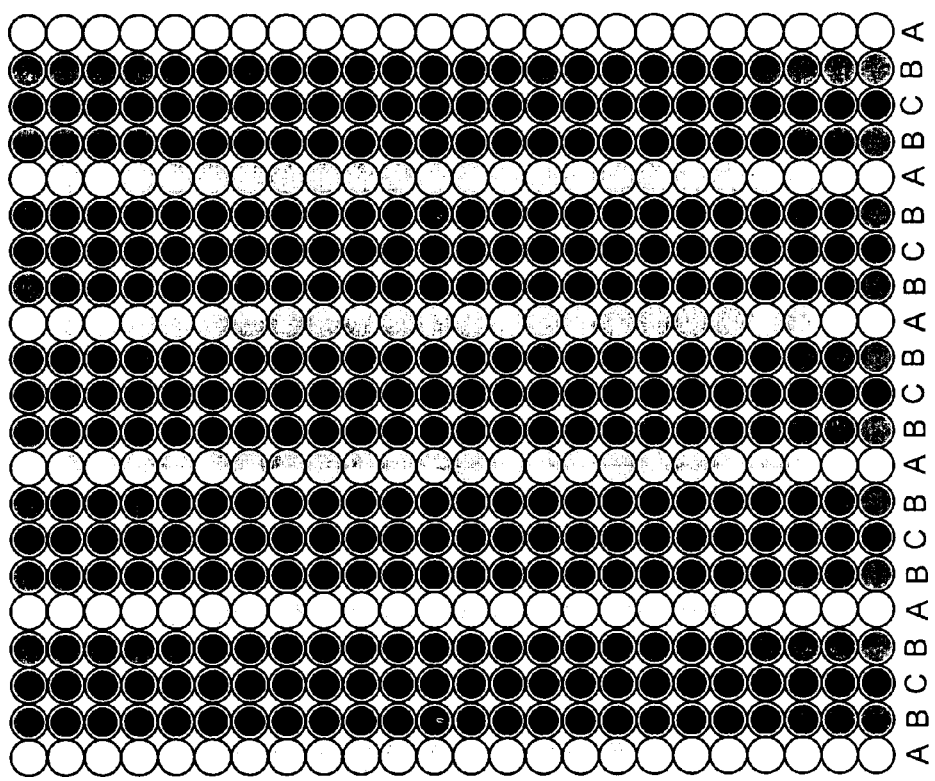
FIG. 26 is a diagram of two-channel optical probe.

Another aspect of the optical probe designs of the present invention is to use more than one channel, where a channel refers to a specific orientation of illumination and collection fibers. Multiple channels can be used in conjunction, either simultaneously or serially, to improve the accuracy of the non-invasive measurements. FIG. 25 is a cross-section diagram of a two-channel sampling subsystem consistent with the design properties of the family of optical probes disclosed in the present invention. In this example, the two channels are measuring the same sample. Therefore, each channel provides a measurement of the same sample from a different perspective. The second perspective provides additional spectroscopic information that helps to decouple the signals due to scattering and absorption. FIG. 26 is a surface view of an optical probe embodiment at the sample interface that shows a pattern of illumination and collection columns (e.g., illumination column A with a proximate collection column B and distal collection column C) consistent with the two-channel sampling subsystem shown in FIG. 25. The channels can also be considered to be oriented in rows, depending on the orientation of observation.

The optical probe design shown in FIGS. 25 and 26 comprise two different channels of collection fibers and one channel of illumination fiber. Designs incorporating two channels of illumination and one channel of collection are equally plausible within the scope of the present invention. Each of the channels can comprise fiber types (illumination or collection) that have a different numerical aperture and spacing. The example in FIGS. 25 and 26 can be extended to include an additional collection channel which creates a four-channel sampling subsystem (two illumination channels and two collection channels yield four combinations). One skilled in the art recognizes the large number of possible multi-channel variants.

Figure 27:
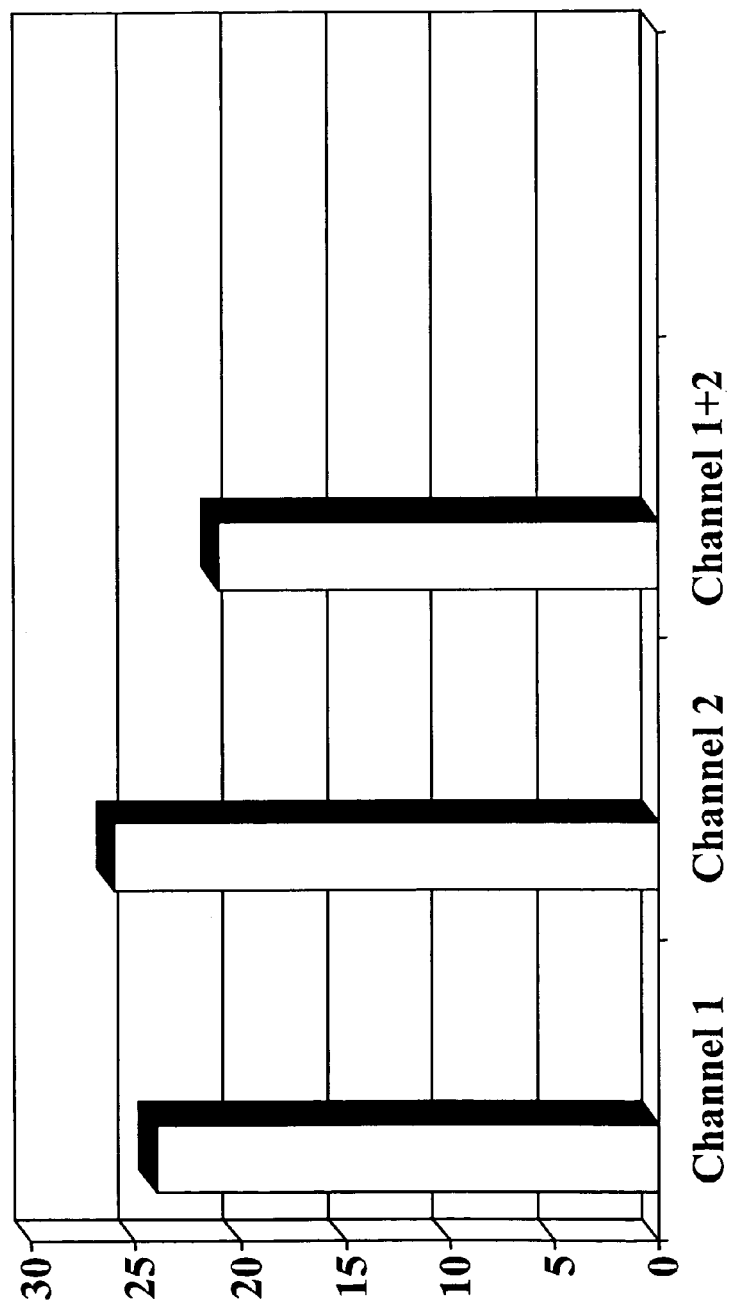
FIG. 27 is a bar chart showing the performance benefit of a multi-channel optical probe.

FIG. 27 is a bar chart of example of the benefits of a multiple channel optical probe that was used for non-invasive glucose measurements. It is clear from FIG. 27 that the combination of the two channels provides superior measurement accuracy when compared to either channel individually. While this example uses two channels, additional channels can provide additional information that can further improve the measurement.

Figure 28:
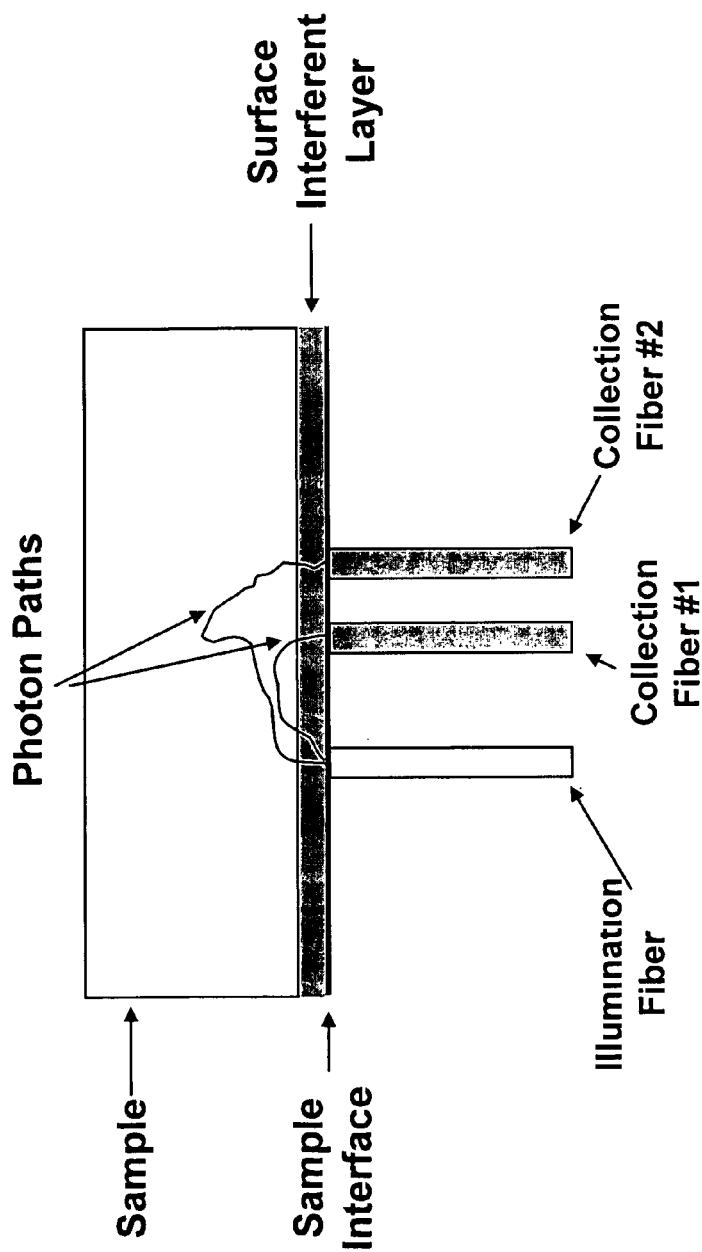
FIG. 28 is a diagram of a two-channel optical probe with a surface interferent.

Another aspect of a multi-channel optical probe is the ability to improve detection and mitigation of surface interferents, such as sweat or lotion, present on the sample. FIG. 28 is a diagram of the photon paths of a two-channel optical probe in the presence of a surface interferent. FIG. 28 shows the tissue interface, a layer of surface interferent, and the sample. In this example, the contribution to each channel's measurement due to the surface interferent is identical. This allows the common surface interferent signal present in both channels to be decoupled from the sample signal that will be different for the two channels.

Non-Invasively Measuring an Analyte Property

The invention can further comprise a method for non-invasively measuring an analyte property in a biological sample of a subject, comprising providing an optical probe, the optical probe comprising a plurality of illumination fibers that deliver source light from an optical probe input to a sample interface, a plurality of collection fibers that deliver light returned from the sample interface to an optical probe output, and wherein the illumination and collection fibers are oriented substantially perpendicular to the sample interface and the illumination and collection fibers are stacked in a plurality of linear rows to provide a stack of fibers arranged in a rectangular pattern and wherein the sample interface is contacted with the biological sample; illuminating the biological sample with the source light delivered by the plurality of illumination fibers from the optical probe input to the sample interface; collecting the light returned from the biological sample to the sample interface and delivering the light returned from the sample interface to the optical probe output; and spectroscopically measuring the returned light from the optical probe output to measure the analyte property.

For example, the analyte can comprise an alcohol, alcohol byproduct, alcohol biomarker, substance of abuse, or a biometric. If the biological sample comprises a forearm of a person, the stack of fibers can form a rectangle such that the long axis of the rectangle is oriented with the forearm at the sample interface that is contacted with the forearm. If the biological sample comprises a finger, the stack of fibers can form a square at the sample interface that is contacted with the finger. The relative spacing, angle, numerical aperture, and placement of the illumination and collection fibers can be arranged to achieve depth targeting in the biological sample. The method can further comprise controlling the temperature of the sample interface. The method can further comprise providing an index matching fluid at the optical interface between the sample and the sample interface to match the optical index of the illumination and collection fibers to the sample. The plurality of illumination fibers can comprise at least two different illumination channels, each illumination channel comprising a plurality of illumination fibers that illuminate the sample with source light from a different perspective than each of the other illumination channels. Alternatively, the plurality of collection fibers can comprise at least two different collection channels, each collection channel comprising a plurality of collection fibers that collect returned light the sample from a different perspective than each of the other collection channels. The at least two different collection channels can comprise a first collection channel comprising rows of collection fibers spaced proximate a row of illumination fibers and a second collection channel comprising rows of collection fibers spaced distal the row of illumination fibers.

EXAMPLE EMBODIMENTS

Figure 29:
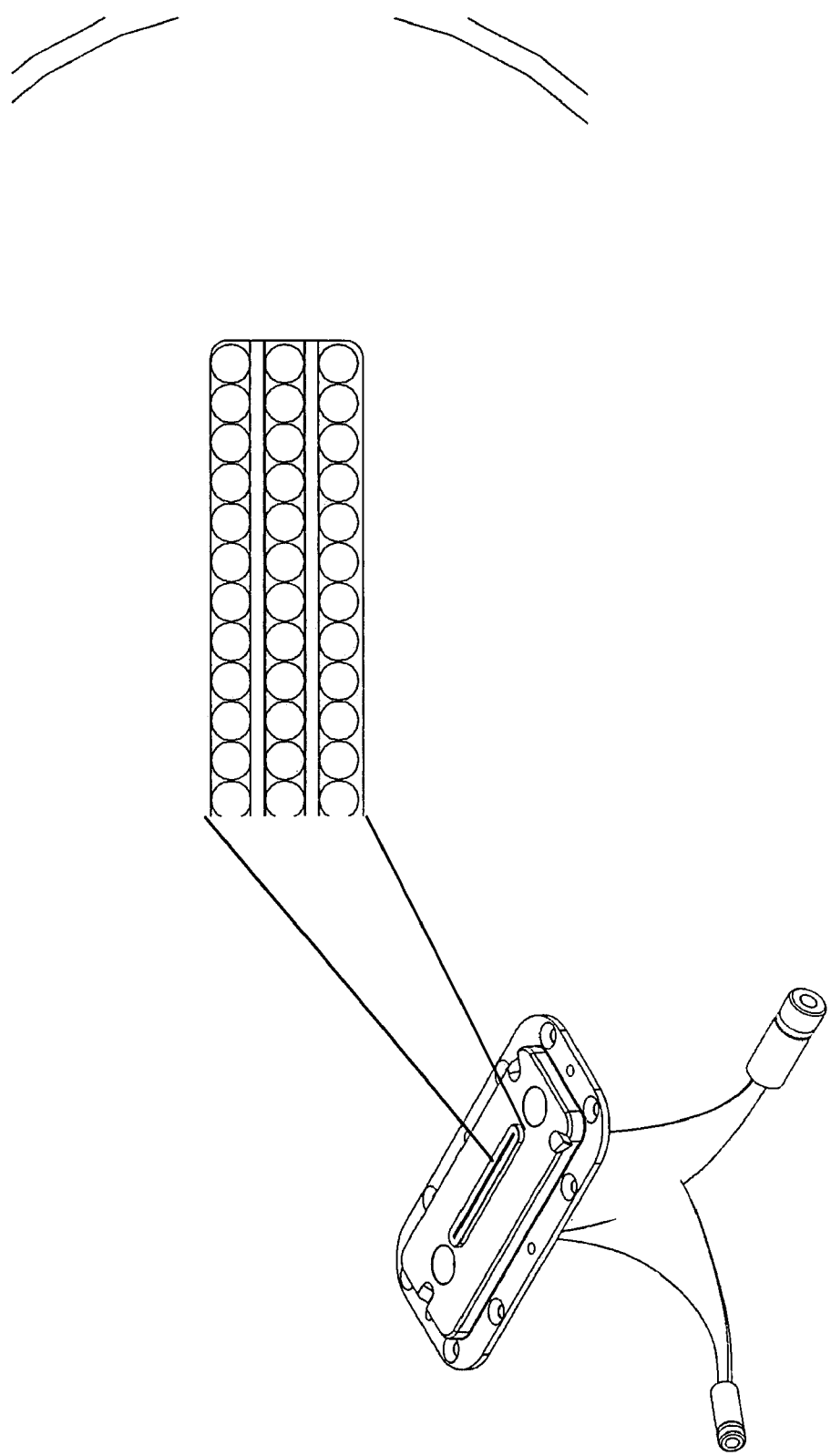
FIG. 29 is a diagram of an optical probe comprising a linear stack of three ribbons with 0.65 NA optical fibers.

FIG. 29 shows a diagram of a preferred embodiment of the present invention that is a linear stack comprised of three ribbons. The outer two ribbons are comprised of illumination fibers while the central ribbon is comprised of collection fibers. An 80-micron spacer is included between each illumination ribbon and the collection ribbon in order to reject unwanted, short-path light. The optical fibers in this design are 0.65 NA silica core, Teflon clad with a core diameter of 200 microns. The illumination fibers are arranged into a circular input ferrule at one end of the optical probe. The collection fibers are arranged into a circular output ferule that is held at approximately 90 degrees to the optical probe input. The spatial locations of the input and output can be in any position consistent with interfacing to the required subsystems.

Figure 30:
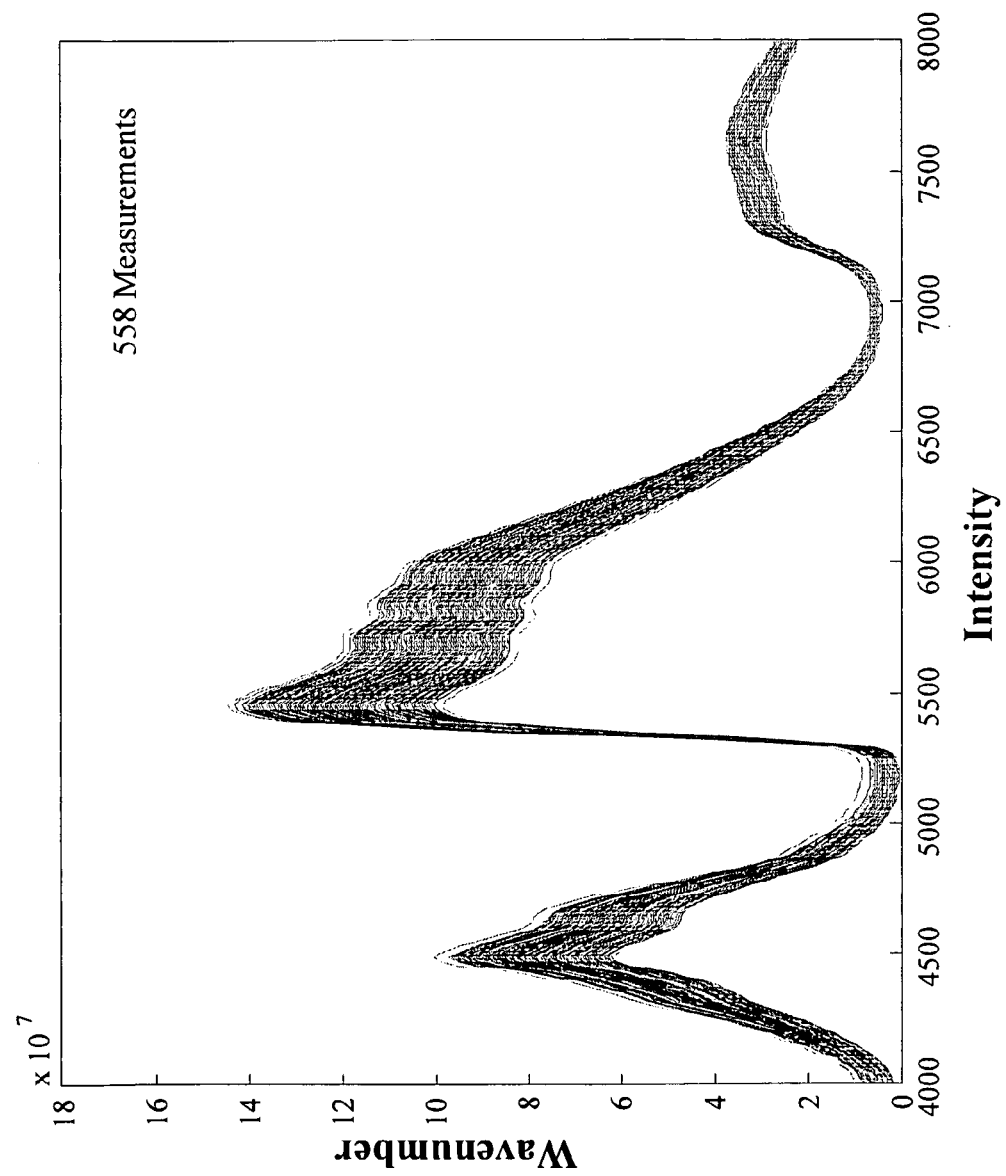
FIG. 30 is a diagram of the non-invasive skin tissue spectra in the near-infrared region obtained using the linear stack of three ribbons optical probe on the forearm.
Figure 31:
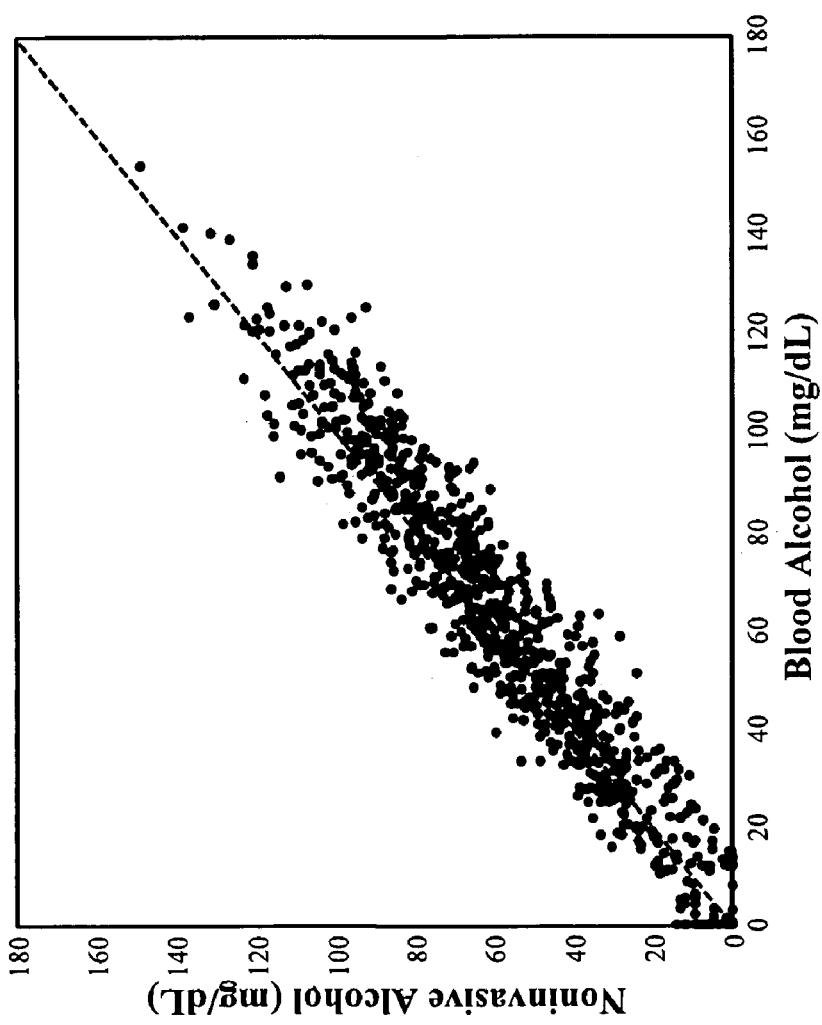
FIG. 31 is a diagram of a linear stack 8:1 optical probe comprising 25 ribbons of 25, 0.37 NA fibers.

FIG. 30 shows non-invasive near-infrared absorbance spectra acquired from forearm tissue using the optical probe shown in FIG. 29. 558 spectroscopic measurements are depicted that span a variety of subjects and environmental conditions. Each measurement demonstrates the absorption of water (e.g., reduced light intensity) at 5200 $cm^{-1}$ and 6900 $cm^{-1}$ which is consistent with the light penetrating the dermal tissue layer of the skin. Dermal penetration is particularly important when measuring analytes or properties of water-bearing layers or compartments. FIG. 31 shows alcohol concentrations obtained from a non-invasive measurement system using the optical probe shown in FIG. 29. The non-invasive measurements acquired from 70 subjects are plotted against their contemporaneous blood alcohol concentrations and show excellent agreement for all of the participants.

Figure 32A:
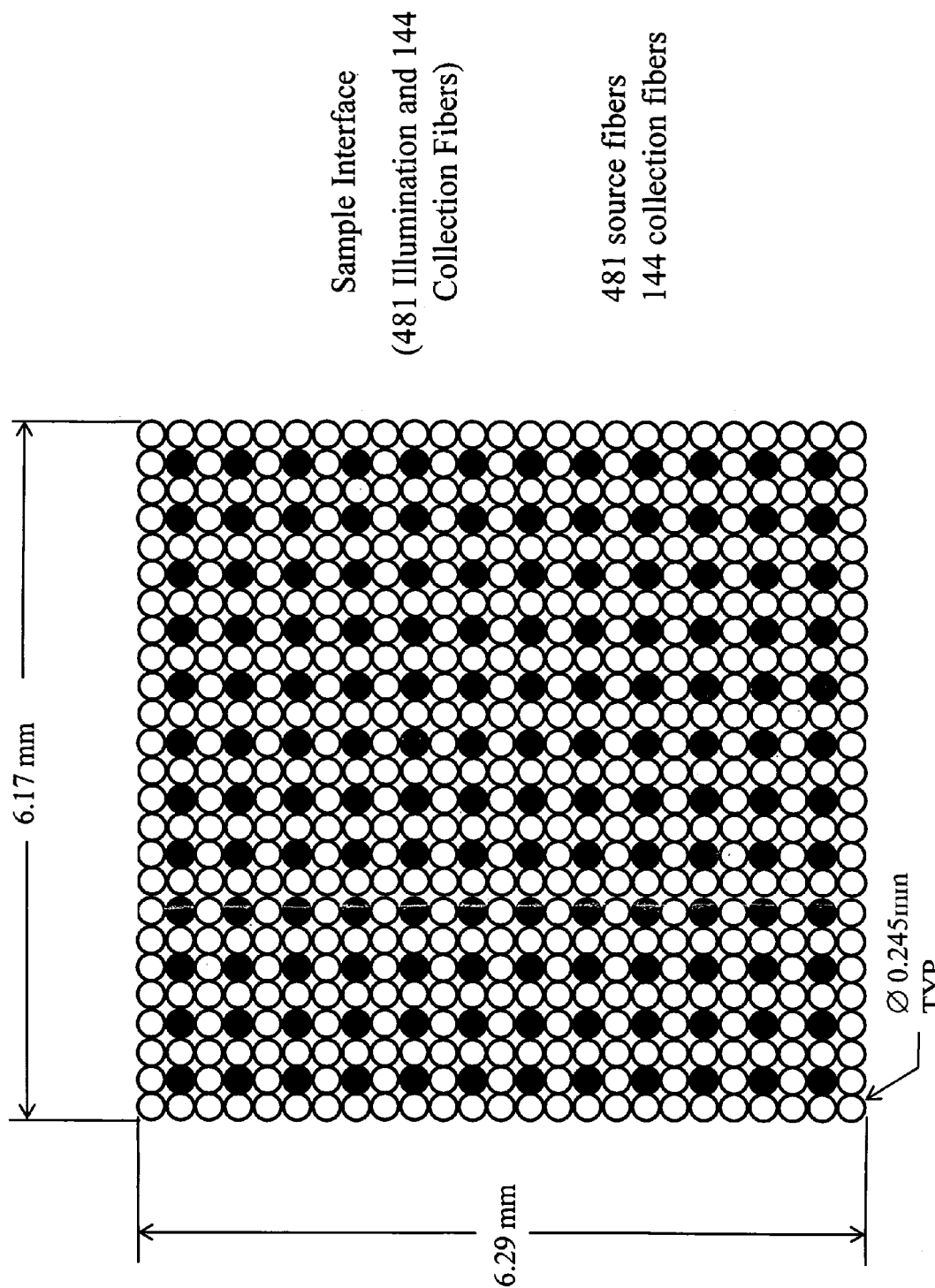
FIG. 32a, 32b, 32c (collectively referred to herein as FIG. 32) comprises a diagram of the non-invasive skin tissue spectra in the near-infrared region obtained using the linear stack 8:1 of 25, 0.37 NA fiber ribbons optical probe on the forearm.
Figure 32B:
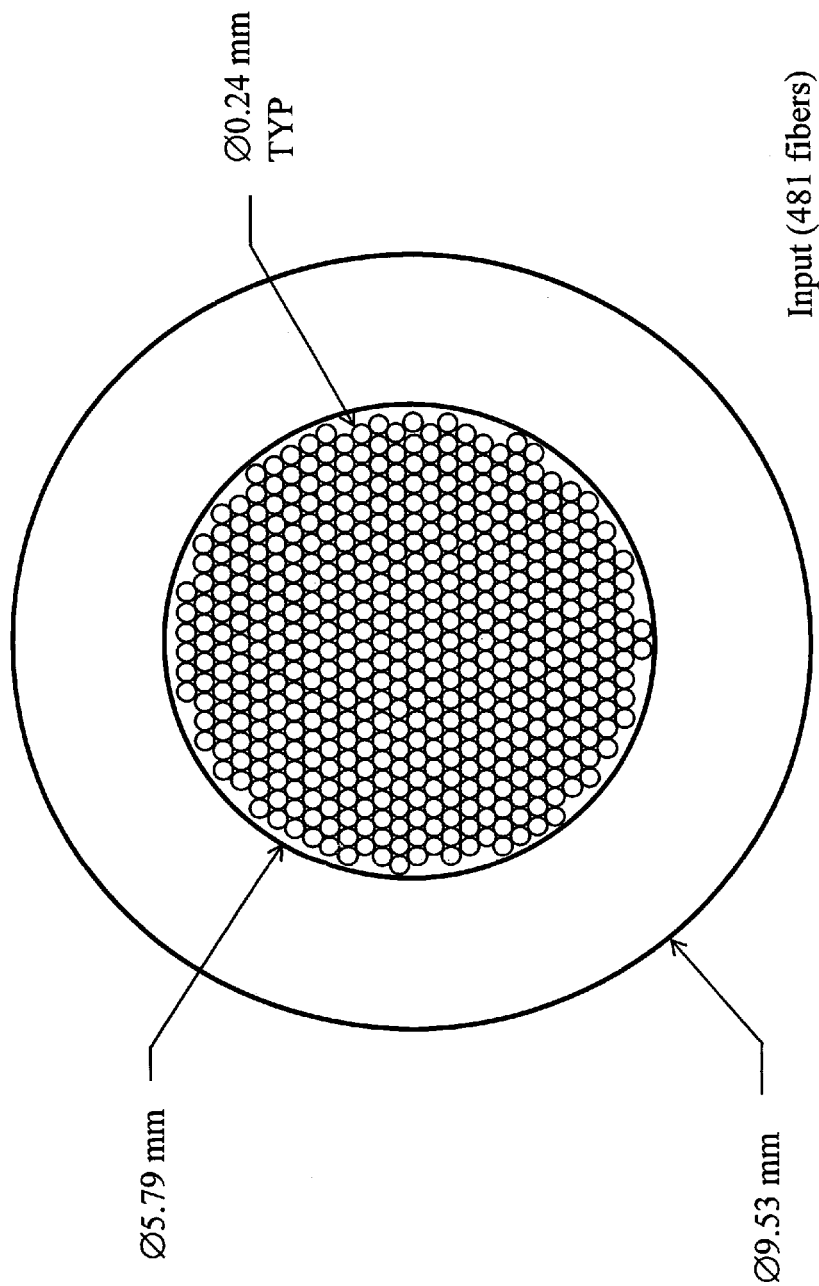
Figure 32C:
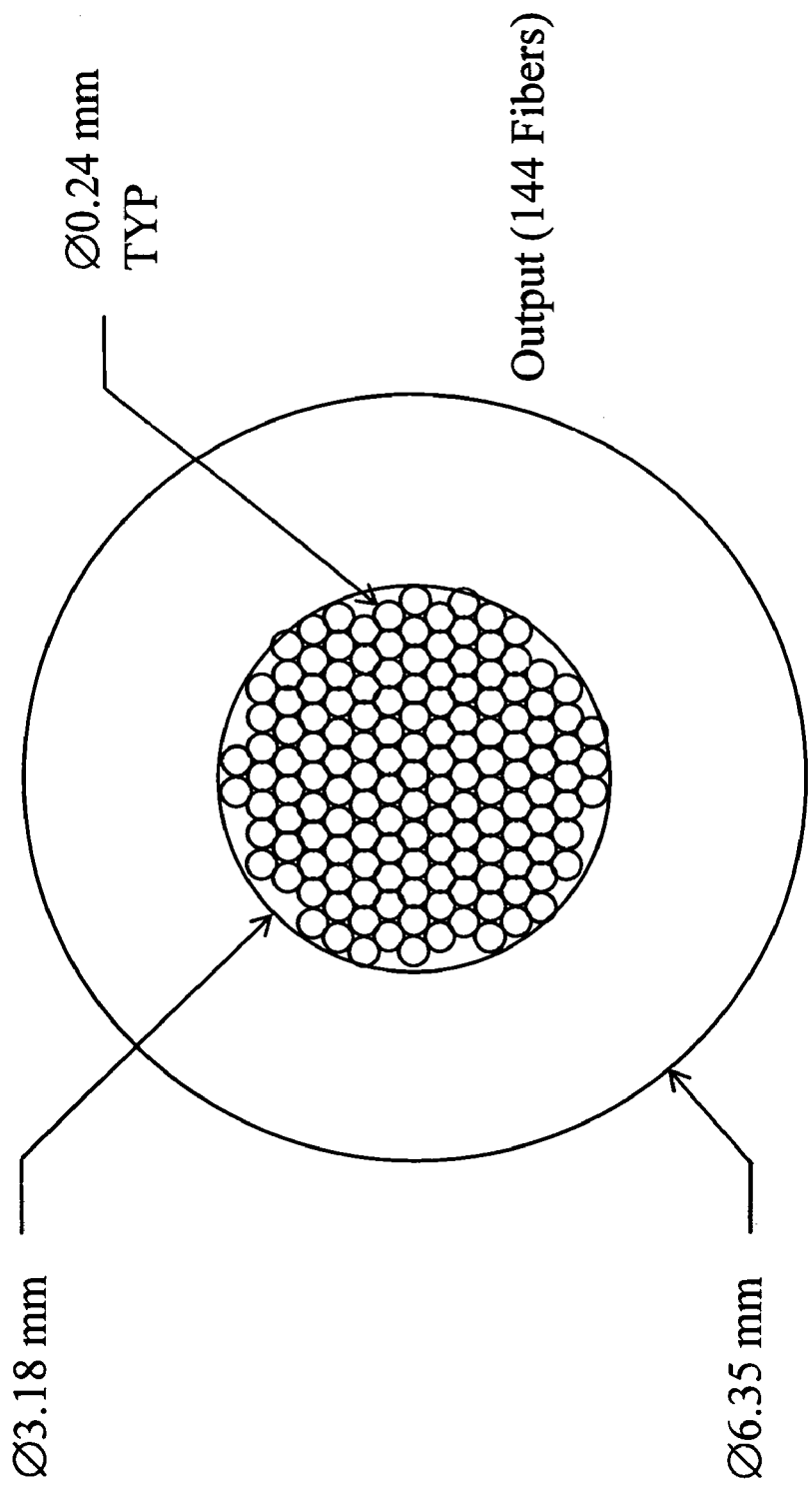

FIG. 32 shows another preferred embodiment comprising 25 ribbons, each ribbon containing 25 optical fibers. The 625 total fibers are separated into 481 illumination fibers and 144 collection fibers. At the sample interface, the fibers are arranged in a linear stack 8:1 configuration. No spacers or gaps are present between the illumination and collection fibers in this embodiment. FIG. 32 also shows cross-section views of the optical probe input and output, which are arranged in a circular geometry. An advantage of this optical probe design is that the sample interface dimensions form an approximately 6.2 mm square, which is useful when measuring small sites, such as fingers or finger tips.

Figure 33:
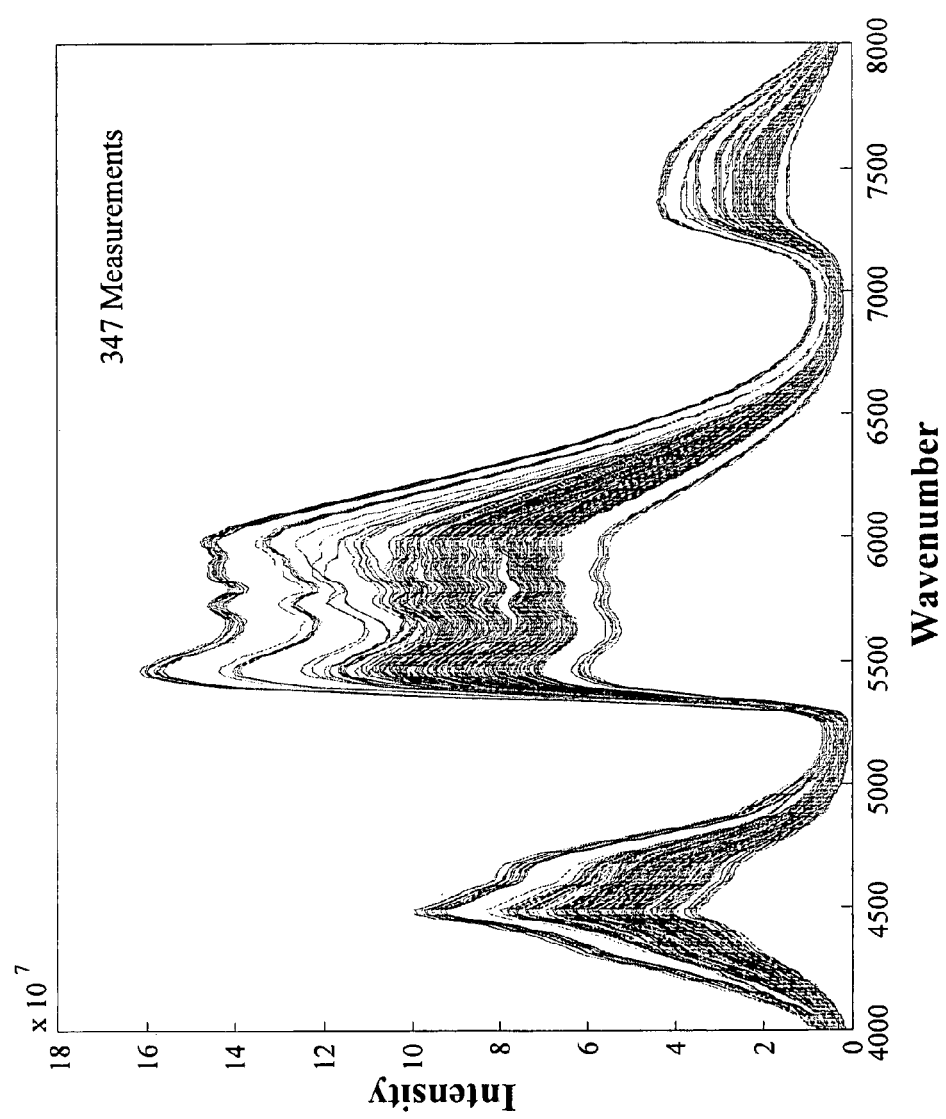
FIG. 33 is a diagram of a linear stack 8:1 optical probe comprising 25 ribbons of 25, 0.22 NA fibers.

FIG. 33 shows 347 non-invasive tissue absorbance spectra acquired from the optical probe design shown in FIG. 32. The optical fibers in this case were 0.37 NA silica core/silica clad with a 200-micron diameter. Similar to the spectra shown in FIG. 30, the absorption of water is clearly present at 5200 $cm^{-1}$ and 6900 $cm^{-1}$ which is consistent with the light penetrating the dermal tissue layer of the skin.

Figure 34:
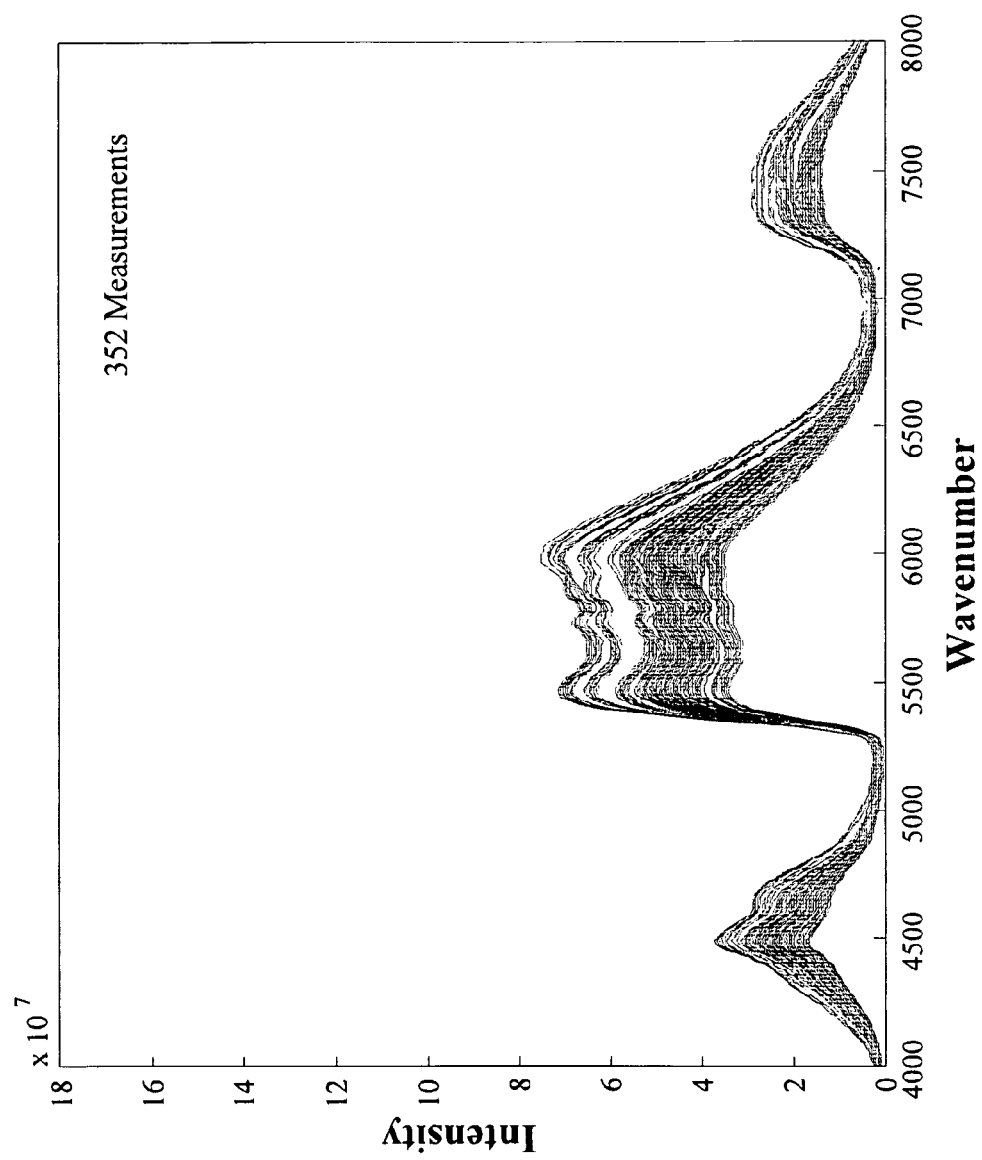
FIG. 34 is a diagram of the non-invasive skin tissue spectra in the near-infrared region obtained using the linear stack 8:1 of 25, 0.22 NA fiber ribbons optical probe on the forearm.

Another preferred embodiment is a variant of the optical probe design of FIG. 33 that has the same sample interface geometry and numbers of input and output optical fibers. However, the optical fibers are 0.22 NA silica core/silica clad with core diameters of 200 microns. FIG. 34 shows 352 non-invasive tissue spectra from the 0.22 NA variant that exhibit similar properties to the spectra shown in FIG. 33.

Figure 35A:
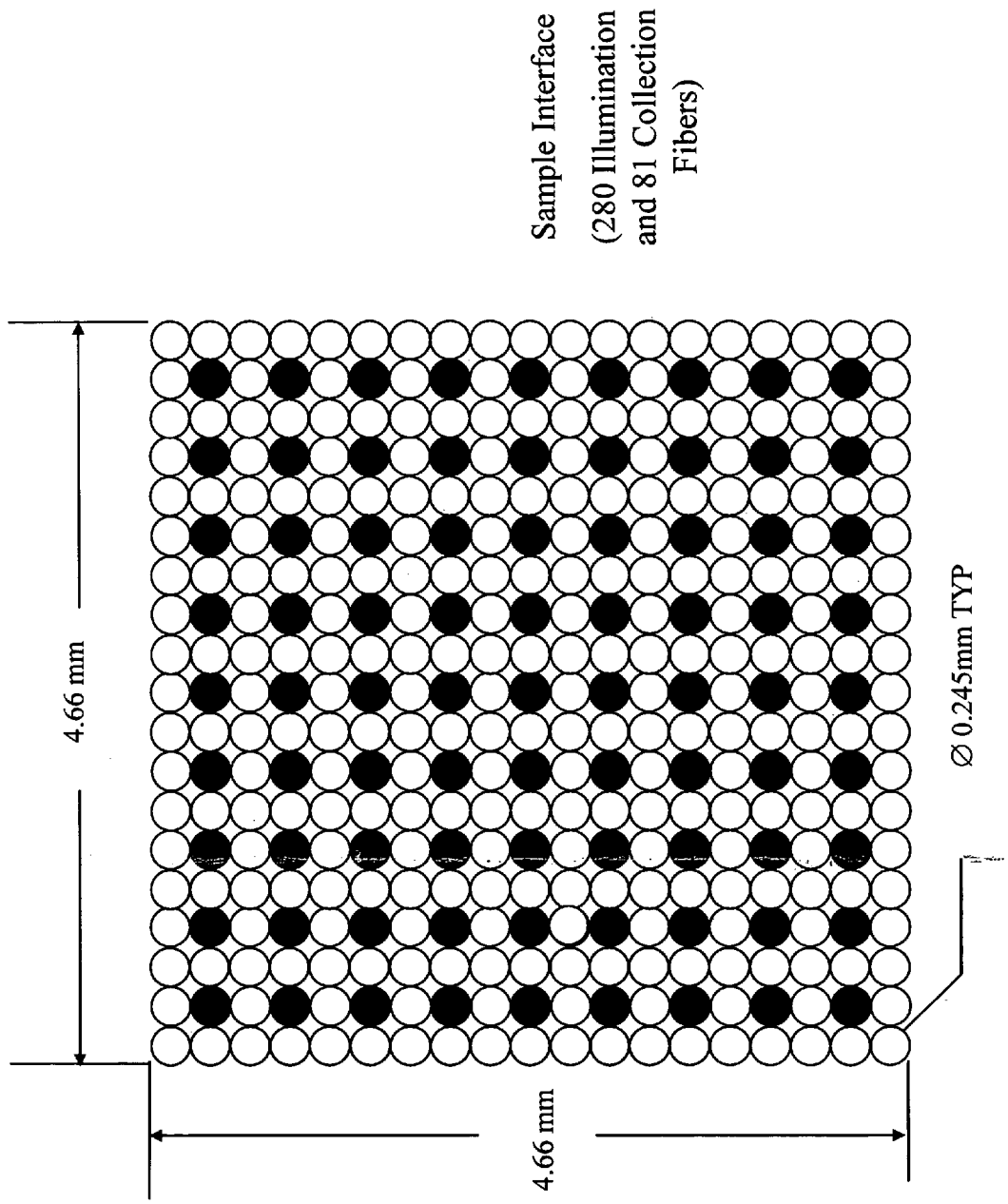
FIG. 35a, 35b, 35c (collectively referred to herein as FIG. 35) comprises a diagram of a linear stack 8:1 optical probe comprising 19 ribbons of 19, 0.37 NA fibers.
Figure 35B:
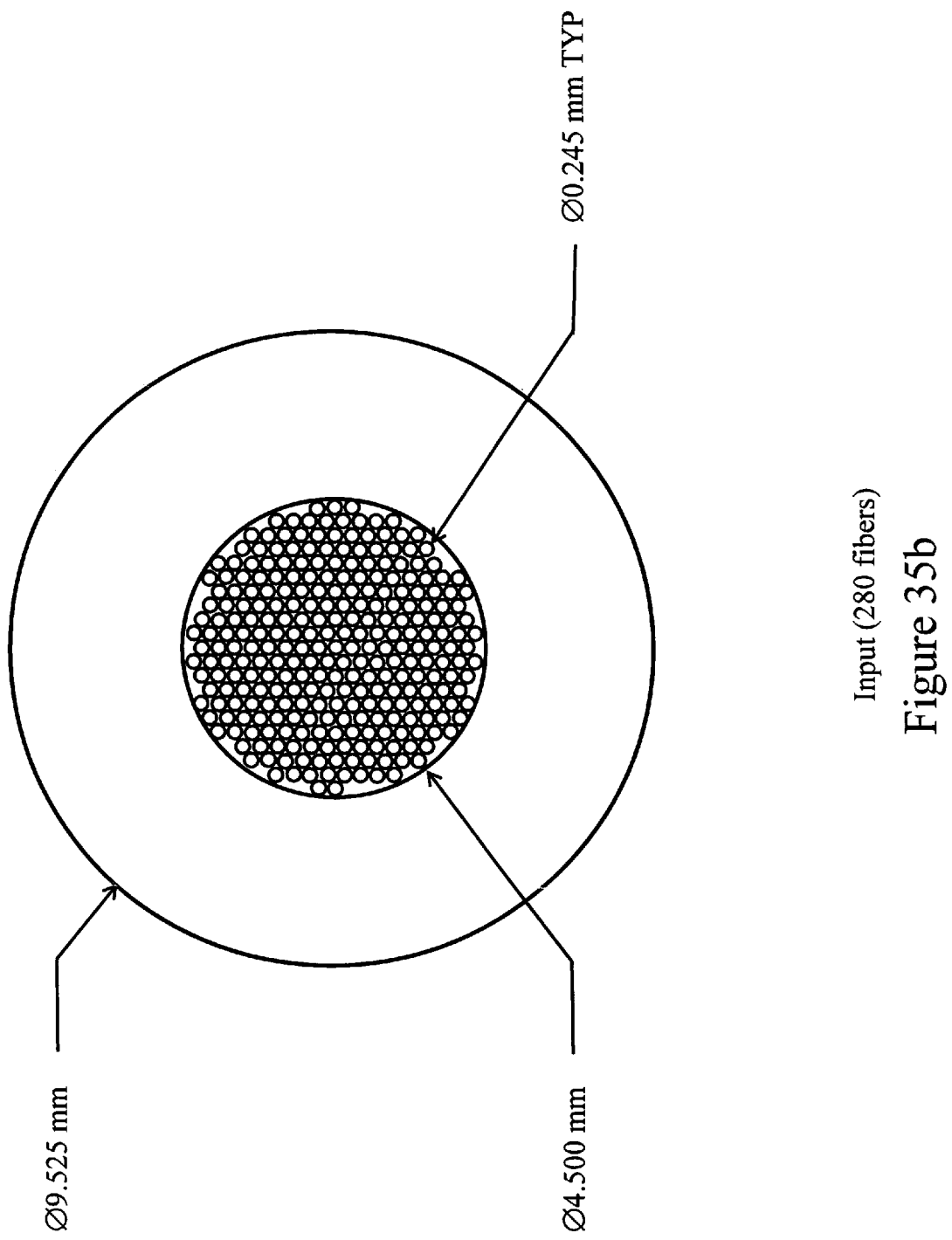
Figure 35C:
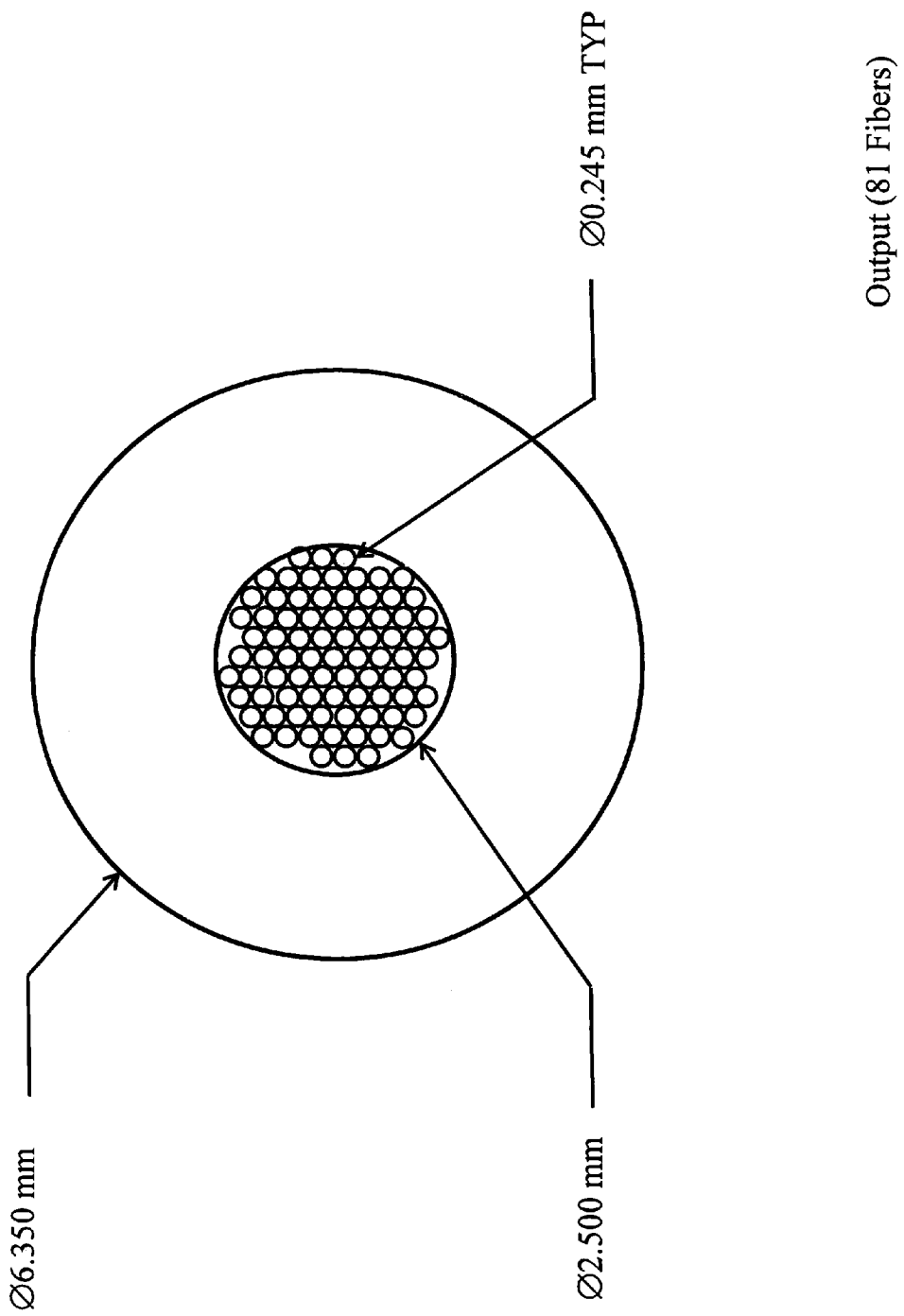
Figure 36A:
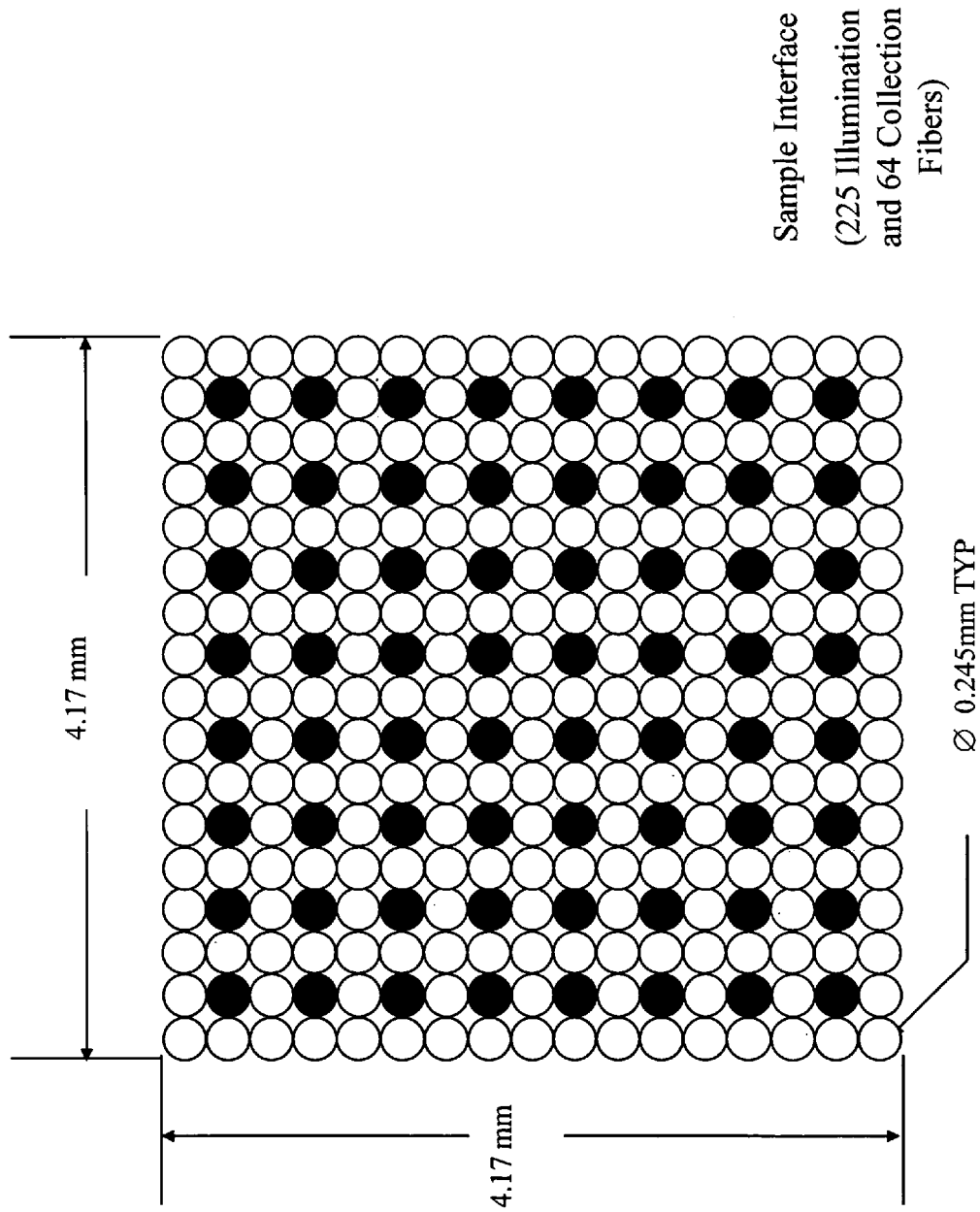
FIG. 36a, 36b, 36c (collectively referred to herein as FIG. 36) comprises a diagram of a linear stack 8:1 optical probe comprising 17 ribbons of 17, 0.44 NA fibers.
Figure 36B:
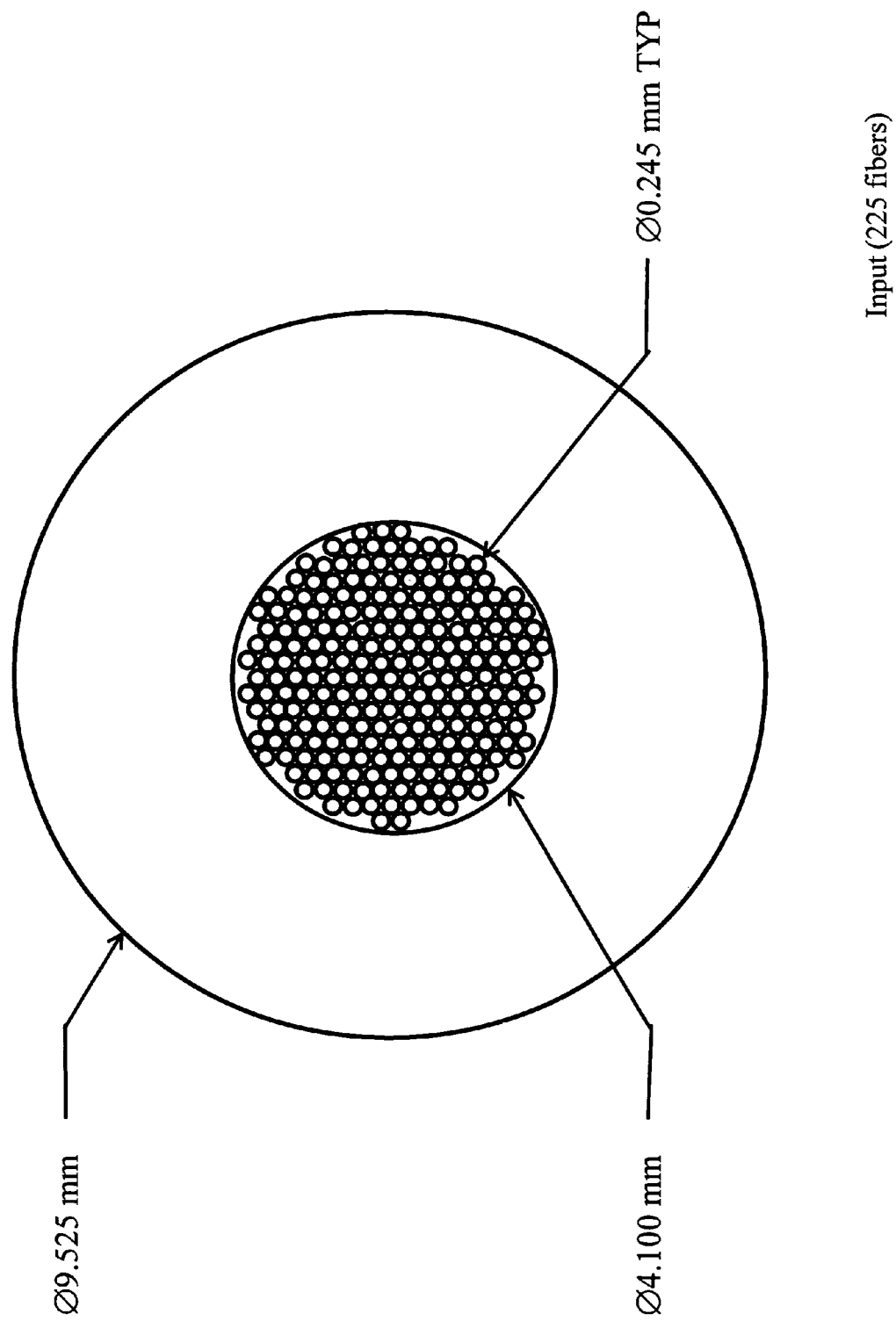
Figure 36C:
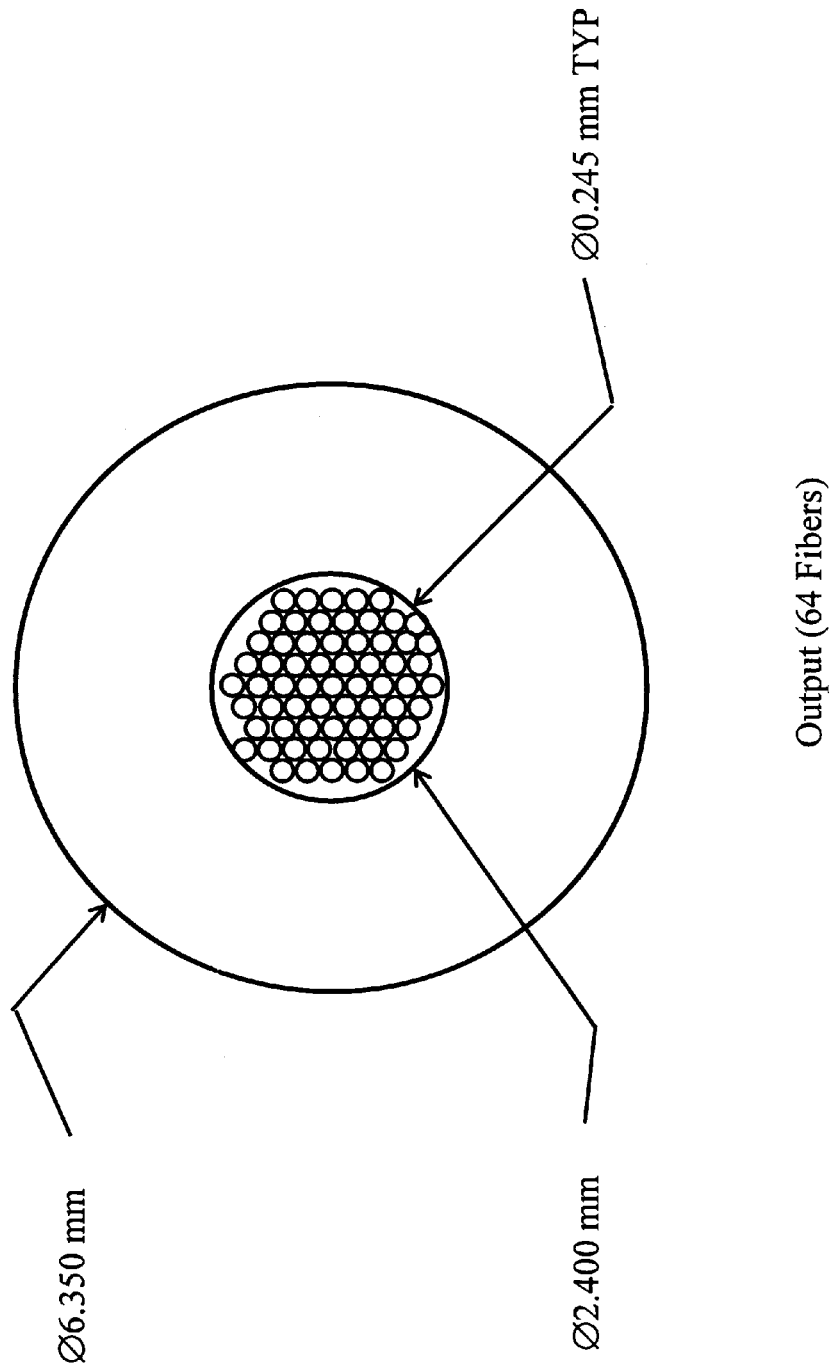

FIGS. 35 and 36 show additional preferred embodiments of the linear stack 8:1 family of optical probe designs. These embodiments have fewer total fibers and correspondingly smaller sample interface sizes. The design depicted in FIG. 35 uses 0.37 NA silica core/silica clad fibers with 200-micron core diameter while the design in FIG. 36 uses 0.44 NA silica core/silica clad fibers with 200-micron core diameter.

An optical probe for non-invasively measuring an analyte property in a biological sample of a subject can comprise: a plurality of illumination fibers that deliver source light from an optical probe input to a sample interface; a plurality of collection fibers that deliver light returned from the sample interface to an optical probe output, and wherein the illumination and collection fibers are oriented substantially perpendicular to the sample interface and the illumination and collection fibers are stacked in a plurality of linear rows to provide a stack of fibers. In such a probe, the stack of fibers can form a rectangle. In such a probe, the stack of fibers can form a square. In such a probe, the illumination and collection fibers can comprise separate rows in the stack of fibers. In such a probe, the illumination and collection fibers can comprise alternating separate rows in the stack of fibers thereby providing a linear stack of fibers. In such a probe, every other row in the stack of fibers can consist of illumination fibers and the intervening rows comprise both illumination and collection fibers. In such a probe, the intervening rows can comprise alternating illumination and collection fibers such that each collection fiber has eight adjacent illumination fibers thereby providing a linear stack 8:1 of fibers. In such a probe, each linear row can comprise alternating illumination and collection fibers such that each collection fiber has four adjacent illumination fibers thereby providing an alternating linear stack of fibers. Such a probe can further comprise an optical homogenizer at the optical probe input to homogenize the source light at the input of the illumination fibers. Such a probe can further comprise an optical homogenizer at the optical probe output to homogenize the return light at the output of the collection fibers. Such a probe can further comprise an aperture at the output of the optical homogenizer to reduce the size of the optical probe output. In such a probe, the numerical aperture of the illumination fibers can be different than the numerical aperture of the collection fibers. In such a probe, the illumination and collection fibers can comprise a silica core and a cladding comprises fused silica, doped silica, Teflon, or a fluoropolymer. In such a probe, the relative spacing, angle, numerical aperture, and placement of the illumination and collection fibers can be arranged to achieve depth targeting. Such a probe can further comprise means to control the temperature of the sample interface. Such a probe can further comprise an index matching fluid at the optical interface between the sample and the sample interface to match the optical index of the illumination and collection fibers to the sample. In such a probe, the plurality of illumination fibers can comprise at least two different illumination channels, each illumination channel comprising a plurality of illumination fibers that illuminate the sample with source light from a different perspective than each of the other illumination channels. In such a probe, the plurality of collection fibers can comprise at least two different collection channels, each collection channel comprising a plurality of collection fibers that collect returned light the sample from a different perspective than each of the other collection channels. In such a probe, the at least two different collection channels can comprise a first collection channel comprising rows of collection fibers spaced proximate a row of illumination fibers and a second collection channel comprising rows of collection fibers spaced distal the row of illumination fibers.

A method according to the present invention for fabricating an optical probe can comprise: fabricating a plurality of ribbons of optical fibers wherein each ribbon comprises a plurality of optical fibers and wherein the optical fibers comprise illumination or collection fibers; verifying at least one parameter of each ribbon to determine the suitability of each ribbon for inclusion in the optical probe; stacking the verified suitable ribbons to form a sample interface comprising linear rows of the stacked ribbons; verifying at least one parameter of the stacked ribbons to determine the suitability of the sample interface; polishing the surface of the sample interface; and verifying at least one parameter of the sample interface to determine the suitability of the polished sample interface. In such a method, the at least one parameter of the ribbon verifying step can comprise determining the presence of adhesive in undesirable locations, the number of broken or poorly transmitting fibers, or the length of the ribbons. In such a method, the at least one parameter of the stacked ribbons verifying step can comprise the alignment of the fibers across the ribbons in the stacks, the presence of adhesive in undesired locations, the number of broken or poorly transmitting fibers, or the overall size and geometry of the linear rows at the sample interface. In such a method, the at least one parameter of the sample interface verifying step can comprise the flatness of the surface of the polished sample interface, the number and size of defects in the surface, the overall smoothness of the surface, or the number of broken or poorly transmitting fibers. Such a method can further comprise separating the illumination fibers into an input group and the collection fibers into an output group after the step of verifying the polished sample interface, and verifying at least one parameter of the separated input and output groups to determine the suitability of the input and output arrangement of the optical probe. In such a method, the separating step can comprise illuminating the end of each fiber opposite the sample interface and observing the location of that fiber at the sample interface. In such a method, the separating step can comprise applying a mask to the sample interface to block all of the illumination or collection fibers, illuminating all of the unmasked fibers, and observing the unmasked fibers that transmit light to the end of the fiber opposite the sample interface. In such a method, the separating step can comprise illuminating the ends of the illuminating fibers opposite the sample interface with one color of light and illuminating the ends of the collecting fibers opposite the sample interface with another color of light and acquiring one or more color or grayscale images of the sample interface. Such a method can further comprise verifying at least one parameter of the arrangement of the optical probe. In such a method, the at least one parameter of the optical probe arrangement verifying step can comprise the number of broken or poorly transmitting fibers, the number of input and output fibers, or the arrangement of the illumination and collection fibers at the sample interface. Such a method can further comprise fabricating an optical probe input comprising the input group of illumination fibers. Such a method can further comprise fabricating an optical probe output comprising the output group of collection fibers.

A method according to the present invention for non-invasively measuring an analyte property in a biological sample of a subject can comprise providing an optical probe such as any of the probes described herein; disposing the optical probe in an operative relationship with the biological sample; illuminating the biological sample with source light delivered by the plurality of illumination fibers from the optical probe input to the sample interface; collecting light returned from the biological sample to the sample interface and delivering the collected light to the optical probe output; and analyzing the returned light from the optical probe output to measure the analyte property. In such a method, the analyte can comprise an alcohol, alcohol byproduct, alcohol biomarker, substance of abuse, or biometric, or a combination thereof. In such a method, the biological sample of a subject can comprise a forearm of a person and wherein the stack of fibers forms a rectangle such that the long axis of the rectangle is oriented with the forearm at the sample interface that is contacted with the forearm. In such a method, the biological sample of a subject comprises a finger of a person and wherein the stack of fibers forms a square at the sample interface that is contacted with the finger. In such a method, the relative spacing, angle, numerical aperture, and placement of the illumination and collection fibers are arranged to achieve depth targeting in the biological sample. Such a method can further comprise controlling the temperature of the sample interface. Such a method can further comprise providing an index matching fluid at the optical interface between the sample and the sample interface to match the optical index of the illumination and collection fibers to the sample. In such a method, the plurality of illumination fibers can comprise at least two different illumination channels, each illumination channel comprising a plurality of illumination fibers that illuminate the sample with source light from a different perspective than each of the other illumination channels. In such a method, the plurality of collection fibers can comprise at least two different collection channels, each collection channel comprising a plurality of collection fibers that collect returned light the sample from a different perspective than each of the other collection channels. In such a method, at least two different collection channels can comprise a first collection channel comprising rows of collection fibers spaced proximate a row of illumination fibers and a second collection channel comprising rows of collection fibers spaced distal the row of illumination fibers.

An analyte measurement system according to the present invention can comprise an optical probe such as any of those described herein; an illumination system adapted to supply light to the optical probe input; a detection system adapted to detect light from the optical probe output; and an analysis system adapted to determine an analyte property from the detected light.

What is claimed is:

1. A method for fabricating an optical probe, comprising:
   fabricating a plurality of ribbons of optical fibers wherein each ribbon comprises a plurality of optical fibers and wherein the optical fibers comprise illumination or collection fibers,
   verifying at least one parameter of each ribbon to determine the suitability of each ribbon for inclusion in the optical probe,
   stacking the verified suitable ribbons to form a sample interface comprising linear rows of the stacked ribbons,
   verifying at least one parameter of the stacked ribbons to determine the suitability of the sample interface,
   polishing the surface of the sample interface, and
   verifying at least one parameter of the sample interface to determine the suitability of the polished sample interface.

2. The method of claim 1, wherein the at least one parameter of the ribbon verifying step comprises determining the presence of adhesive in undesirable locations, the number of broken or poorly transmitting fibers, or the length of the ribbons.

3. The method of claim 1, wherein the at least one parameter of the stacked ribbons verifying step comprises the alignment of the fibers across the ribbons in the stacks, the presence of adhesive in undesired locations, the number of broken or poorly transmitting fibers, or the overall size and geometry of the linear rows at the sample interface.

4. The method of claim 1, wherein the at least one parameter of the sample interface verifying step comprises the flatness of the surface of the polished sample interface, the number and size of defects in the surface, the overall smoothness of the surface, or the number of broken or poorly transmitting fibers.

5. The method of claim 1, further comprising separating the illumination fibers into an input group and the collection fibers into an output group after the step of verifying the polished sample interface, and verifying at least one parameter of the separated input and output groups to determine the suitability of the input and output arrangement of the optical probe.

6. The method of claim 5, wherein the separating step comprises illuminating the end of each fiber opposite the sample interface and observing the location of that fiber at the sample interface.

7. The method of claim 5, wherein the separating step comprises applying a mask to the sample interface to block all of the illumination or collection fibers, illuminating all of the unmasked fibers, and observing the unmasked fibers that transmit light to the end of the fiber opposite the sample interface.

8. The method of claim 5, wherein the separating step comprises illuminating the ends of the illuminating fibers opposite the sample interface with one color of light and illuminating the ends of the collecting fibers opposite the sample interface with another color of light and acquiring one or more color or grayscale images of the sample interface.

9. The method of claim 5, further comprising verifying at least one parameter of the arrangement of the optical probe.

10. The method of claim 9, wherein the at least one parameter of the optical probe arrangement verifying step comprises the number of broken or poorly transmitting fibers, the number of input and output fibers, or the arrangement of the illumination and collection fibers at the sample interface.

11. The method of claim 5, further comprising fabricating an optical probe input comprising the input group of illumination fibers.

12. The method of claim 5, further comprising fabricating an optical probe output comprising the output group of collection fibers.

13. A method as in claim 1, wherein stacking the verified suitable ribbons comprises forming a rectangular stack.

14. A method as in claim 1, wherein stacking the verified suitable ribbons comprises forming a square stack.

15. A method as in claim 1, where stacking the verified suitable ribbons comprises alternating separate rows in the stack of fibers thereby providing a linear stack of fibers.

16. A method as in claim 1, where stacking the verified suitable ribbons comprises forming a stack such that every other row in the stack of fibers consists of illumination fibers and the intervening rows comprise both illumination and collection fibers.

17. A method as in claim 1, where stacking the verified suitable ribbons comprises forming a stack such that the intervening rows comprise alternating illumination and collection fibers such that each collection fiber has eight adjacent illumination fibers thereby providing a linear stack 8:1 of fibers.

18. A method as in claim 17, where stacking the verified suitable ribbons comprises forming a stack such that each linear row comprises alternating illumination and collection fibers such that each collection fiber has four adjacent illumination fibers thereby providing an alternating linear stack of fibers.

19. A method as in claim 1, further comprising mounting one or more optical homogenizers at the optical probe input, the optical probe output, or both.

20. A method for making an analyte measurement system, comprising:
   a. Providing an optical probe made according to the method of claim 1;
   b. Providing an illumination system, and placing the illumination system in operative relationship with the optical probe input;
   c. Providing a detection system, and placing the detection system in operative relationship with the optical probe output; and
   d. Providing an analysis system, and placing the analysis system in operative relationship with the detection system.

* * * * *